United States Patent
Fouts et al.

(10) Patent No.: US 12,256,996 B2
(45) Date of Patent: Mar. 25, 2025

(54) SYSTEMS AND METHODS FOR GENERATING A THREE-DIMENSIONAL MODEL OF A JOINT FROM TWO-DIMENSIONAL IMAGES

(71) Applicant: Stryker Corporation, Kalamazoo, MI (US)

(72) Inventors: Brian Fouts, Morgan Hill, CA (US); Jakob Kemper, Heemstede (NL); Heiko Michael Gottschling, Munich (DE); Manuel Schroeder, Ellingen (DE)

(73) Assignee: Stryker Corporation, Portage, MI (US)

( * ) Notice: Subject to any disclaimer, the term of this patent is extended or adjusted under 35 U.S.C. 154(b) by 519 days.

(21) Appl. No.: 17/644,335

(22) Filed: Dec. 14, 2021

(65) Prior Publication Data
US 2022/0183760 A1 Jun. 16, 2022

Related U.S. Application Data

(60) Provisional application No. 63/125,932, filed on Dec. 15, 2020.

(51) Int. Cl.
*A61B 34/10* (2016.01)
*A61B 90/00* (2016.01)
(Continued)

(52) U.S. Cl.
CPC .............. *A61B 34/10* (2016.02); *A61B 90/37* (2016.02); *G06T 7/0012* (2013.01); *G06T 7/32* (2017.01);
(Continued)

(58) Field of Classification Search
CPC ... A61B 34/10; A61B 90/37; A61B 2034/105; A61B 2090/374; A61B 2090/3764;
(Continued)

(56) References Cited

U.S. PATENT DOCUMENTS

| 5,437,672 A | 8/1995 | Alleyne |
| 5,862,249 A | 1/1999 | Jang et al. |

(Continued)

FOREIGN PATENT DOCUMENTS

| CN | 101518447 A | 9/2009 |
| CN | 102194047 A | 9/2011 |

(Continued)

OTHER PUBLICATIONS

Fouts et al., U.S. Advisory Action dated Aug. 9, 2024, directed to U.S. Appl. No. 18/190,956; 6 pages.

(Continued)

*Primary Examiner* — Juan A Torres
(74) *Attorney, Agent, or Firm* — Morrison & Foerster LLP

(57) ABSTRACT

A method for modeling a joint before, during, and/or after a medical procedure includes receiving first imaging data capturing the joint from a first imaging perspective and second imaging data capturing the joint from a second imaging perspective that is different than the first imaging perspective, the first and second imaging data generated intraoperatively via a two-dimensional imaging modality, generating three-dimensional image data by back-projecting the first and second imaging data in three-dimensional space in accordance with a relative difference between the first and second imaging perspectives, generating a three-dimensional model of the joint based on processing the three-dimensional image data with a machine learning model trained on imaging data generated via at least a three-dimensional imaging modality, and displaying a visualization based on the three-dimensional model of the joint during the medical procedure.

29 Claims, 14 Drawing Sheets

(51) Int. Cl.
   *G06T 7/00* (2017.01)
   *G06T 7/32* (2017.01)
(52) U.S. Cl.
   CPC ... *A61B 2034/105* (2016.02); *A61B 2090/374* (2016.02); *A61B 2090/3764* (2016.02); *G06T 2207/10028* (2013.01); *G06T 2207/10081* (2013.01); *G06T 2207/10088* (2013.01); *G06T 2207/10121* (2013.01); *G06T 2207/20081* (2013.01); *G06T 2207/20084* (2013.01); *G06T 2207/30008* (2013.01)
(58) Field of Classification Search
   CPC ... A61B 2090/367; G06T 7/0012; G06T 7/32; G06T 2207/10028; G06T 2207/10081; G06T 2207/10088; G06T 2207/10121; G06T 2207/20081; G06T 2207/20084; G06T 2207/30008; G16H 50/20; G16H 20/40
   USPC .......................................... 382/128
   See application file for complete search history.

(56) References Cited

U.S. PATENT DOCUMENTS

| | | |
|---|---|---|
| 6,161,080 A | 12/2000 | Aouni-Ateshian et al. |
| 6,205,411 B1 | 3/2001 | Digioia, III et al. |
| 6,697,664 B2 | 2/2004 | Kienzle, III et al. |
| 7,167,738 B2 | 1/2007 | Schweikard et al. |
| 7,231,076 B2 | 6/2007 | Fu et al. |
| 7,327,865 B2 | 2/2008 | Fu et al. |
| 7,643,862 B2 | 1/2010 | Schoenefeld |
| 7,689,042 B2 | 3/2010 | Brunner et al. |
| 7,783,008 B2 | 8/2010 | Jabri |
| 7,949,386 B2 | 5/2011 | Buly et al. |
| 8,014,984 B2 | 9/2011 | Iannotti et al. |
| 8,052,623 B2 | 11/2011 | Haimerl et al. |
| 8,090,166 B2 | 1/2012 | Rappaport et al. |
| 8,152,816 B2 | 4/2012 | Tuma et al. |
| 8,328,816 B2 | 12/2012 | Beaule |
| 8,369,593 B2 | 2/2013 | Peng et al. |
| 8,594,397 B2 | 11/2013 | Haimerl et al. |
| 8,611,697 B2 | 12/2013 | Nathaniel et al. |
| 8,678,125 B2 | 3/2014 | Kosugi et al. |
| 8,679,125 B2 | 3/2014 | Smith et al. |
| 8,694,075 B2 | 4/2014 | Groszmann |
| 8,696,603 B2 | 4/2014 | Takahashi et al. |
| 8,702,805 B2 | 4/2014 | Trabish |
| 8,715,289 B2 | 5/2014 | Smith |
| 8,774,900 B2 | 7/2014 | Buly et al. |
| 8,828,009 B2 | 9/2014 | Allen et al. |
| 8,831,324 B2 | 9/2014 | Penenberg |
| 8,858,563 B2 | 10/2014 | Philippon et al. |
| 8,888,782 B2 | 11/2014 | Smith et al. |
| 8,890,511 B2 | 11/2014 | Belew |
| 8,900,320 B2 | 12/2014 | Frederick et al. |
| 8,923,584 B2 | 12/2014 | Chabanas et al. |
| 8,934,961 B2 | 1/2015 | Lakin et al. |
| 8,958,611 B2 | 2/2015 | Ikits |
| 8,965,108 B2 | 2/2015 | Chabanas et al. |
| 9,020,223 B2 | 4/2015 | Chabanas et al. |
| 9,082,319 B2 | 7/2015 | Shimada et al. |
| 9,113,921 B2 | 8/2015 | Lang et al. |
| 9,113,971 B2 | 8/2015 | Metzger et al. |
| 9,122,670 B2 | 9/2015 | Chabanas et al. |
| 9,123,155 B2 | 9/2015 | Cunningham et al. |
| 9,173,716 B2 | 11/2015 | Kasodekar et al. |
| 9,183,629 B2 | 11/2015 | Chabanas et al. |
| 9,220,567 B2 | 12/2015 | Sutherland et al. |
| 9,271,804 B2 | 3/2016 | Wu |
| 9,320,421 B2 | 4/2016 | Chabanas et al. |
| 9,345,495 B2 | 5/2016 | Gibson et al. |
| 9,345,552 B2 | 5/2016 | Janik et al. |
| 9,386,993 B2 | 7/2016 | Meridew et al. |
| 9,402,726 B2 | 8/2016 | Linderman et al. |
| 9,443,346 B2 | 9/2016 | Ikits |
| 9,480,534 B2 | 11/2016 | Bowling et al. |
| 9,514,533 B2 | 12/2016 | Chabanas et al. |
| 9,672,662 B2 | 6/2017 | Scanlan et al. |
| 10,070,903 B2 | 9/2018 | Blau |
| 10,105,168 B2 | 10/2018 | Blau |
| 10,709,394 B2 | 7/2020 | Zhou et al. |
| 10,918,398 B2 | 2/2021 | Fouts et al. |
| 2003/0176783 A1 | 9/2003 | Hu |
| 2004/0242987 A1 | 12/2004 | Liew et al. |
| 2005/0096535 A1 | 5/2005 | de la Barrera |
| 2007/0016008 A1 | 1/2007 | Schoenefeld |
| 2007/0129630 A1 | 6/2007 | Shimko |
| 2007/0135706 A1 | 6/2007 | Shimko et al. |
| 2007/0249967 A1 | 10/2007 | Buly et al. |
| 2007/0260256 A1 | 11/2007 | Beaule |
| 2008/0039717 A1 | 2/2008 | Frigg et al. |
| 2008/0058641 A1 | 3/2008 | Shimko |
| 2008/0300478 A1 | 12/2008 | Zuhars |
| 2009/0000626 A1 | 1/2009 | Quaid et al. |
| 2009/0209851 A1 | 8/2009 | Blau |
| 2010/0049493 A1 | 2/2010 | Haimerl |
| 2010/0284590 A1 | 11/2010 | Krishnan et al. |
| 2011/0190774 A1 | 8/2011 | Nikolchev et al. |
| 2011/0213374 A1 | 9/2011 | Fitz et al. |
| 2011/0213377 A1 | 9/2011 | Lang et al. |
| 2011/0213379 A1 | 9/2011 | Blau et al. |
| 2011/0213428 A1 | 9/2011 | Fitz et al. |
| 2011/0213429 A1 | 9/2011 | Lang et al. |
| 2011/0238431 A1 | 9/2011 | Cionni et al. |
| 2011/0270295 A1 | 11/2011 | Litvack et al. |
| 2011/0301654 A1 | 12/2011 | Wozencroft et al. |
| 2012/0066892 A1 | 3/2012 | Lang et al. |
| 2012/0271147 A1 | 10/2012 | Kim et al. |
| 2013/0083984 A1 | 4/2013 | Chabanas et al. |
| 2013/0089253 A1 | 4/2013 | Chabanas et al. |
| 2013/0114866 A1 | 5/2013 | Kasodekar et al. |
| 2013/0191099 A1 | 7/2013 | Krekel |
| 2013/0211232 A1 | 8/2013 | Murphy et al. |
| 2013/0211386 A1 | 8/2013 | Blau et al. |
| 2013/0211408 A1 | 8/2013 | Kather et al. |
| 2013/0211531 A1 | 8/2013 | Steines et al. |
| 2013/0314440 A1 | 11/2013 | Simon et al. |
| 2013/0315371 A1 | 11/2013 | Simon et al. |
| 2014/0079303 A1 | 3/2014 | Pfrengle et al. |
| 2014/0187908 A1 | 7/2014 | Ellermann et al. |
| 2014/0243833 A1 | 8/2014 | Smith |
| 2014/0278322 A1 | 9/2014 | Jaramaz et al. |
| 2014/0316417 A1 | 10/2014 | Kaiser et al. |
| 2014/0322197 A1 | 10/2014 | Brooks |
| 2014/0378982 A1 | 12/2014 | Philippon et al. |
| 2015/0066151 A1 | 3/2015 | Frederick et al. |
| 2015/0106024 A1 | 4/2015 | Lightcap et al. |
| 2015/0133945 A1 | 5/2015 | Dushyant et al. |
| 2015/0182295 A1 | 7/2015 | Bozung et al. |
| 2015/0185846 A1 | 7/2015 | Otto et al. |
| 2015/0265266 A1 | 9/2015 | Sanchez et al. |
| 2015/0265362 A1 | 9/2015 | Andersson et al. |
| 2015/0269727 A1 | 9/2015 | Chabanas et al. |
| 2015/0355298 A1 | 12/2015 | Ben-Eliezer et al. |
| 2016/0038160 A1 | 2/2016 | Metzger et al. |
| 2016/0066770 A1 | 3/2016 | Barbato et al. |
| 2016/0074124 A1 | 3/2016 | Fitz et al. |
| 2016/0113720 A1 | 4/2016 | Lavallee et al. |
| 2016/0135816 A1 | 5/2016 | Lavallee et al. |
| 2016/0157751 A1 | 6/2016 | Mahfouz |
| 2016/0157936 A1 | 6/2016 | Netravali |
| 2016/0175054 A1 | 6/2016 | Kang et al. |
| 2016/0191887 A1 | 6/2016 | Casas |
| 2016/0235381 A1 | 8/2016 | Scanlan et al. |
| 2016/0242931 A1 | 8/2016 | Wong et al. |
| 2016/0253846 A1 | 9/2016 | Scanlan et al. |
| 2016/0262772 A1 | 9/2016 | Gibson et al. |
| 2016/0278787 A1 | 9/2016 | Axelson, Jr. et al. |
| 2016/0278793 A1 | 9/2016 | Meridew et al. |
| 2016/0324580 A1 | 11/2016 | Esterberg |
| 2016/0331467 A1 | 11/2016 | Slamin et al. |
| 2017/0306416 A1 | 10/2017 | Bedoya et al. |

(56) References Cited

U.S. PATENT DOCUMENTS

| | | | |
|---|---|---|---|
| 2018/0035964 | A1 | 2/2018 | Funabasama et al. |
| 2018/0318014 | A1 | 11/2018 | Gangwar et al. |
| 2019/0133693 | A1* | 5/2019 | Mahfouz ................. A61B 6/12 |
| 2019/0167221 | A1 | 6/2019 | Simon et al. |
| 2019/0231433 | A1 | 8/2019 | Amanatullah |
| 2019/0231434 | A1* | 8/2019 | Lambers ............. A61F 2/30942 |
| 2020/0253667 | A1 | 8/2020 | Fouts et al. |
| 2020/0312011 | A1* | 10/2020 | Kopeinigg ............ G06T 19/006 |
| 2021/0169503 | A1 | 6/2021 | Fouts et al. |
| 2021/0251590 | A1* | 8/2021 | Guo ........................ A61B 6/466 |
| 2021/0259774 | A1 | 8/2021 | Fouts et al. |
| 2023/0210599 | A1 | 7/2023 | Lambers et al. |
| 2023/0414231 | A1 | 12/2023 | Fouts |

FOREIGN PATENT DOCUMENTS

| | | |
|---|---|---|
| CN | 104185451 A | 12/2014 |
| CN | 104244860 A | 12/2014 |
| CN | 112037200 A | 12/2020 |
| DE | 10057023 A1 | 6/2002 |
| EP | 1844726 B1 | 10/2007 |
| EP | 2618313 A1 | 7/2013 |
| WO | 2011/158117 A2 | 12/2011 |
| WO | 2012/149964 A1 | 11/2012 |
| WO | 2013/174401 A1 | 11/2013 |
| WO | 2013/174402 A1 | 11/2013 |
| WO | 2014/048447 A1 | 4/2014 |
| WO | 2015/124171 A1 | 8/2015 |
| WO | 2016/154557 A1 | 9/2016 |
| WO | 2017218933 A1 | 12/2017 |
| WO | 2018/236936 A1 | 12/2018 |
| WO | 2019/148154 A1 | 8/2019 |

OTHER PUBLICATIONS

Fouts et al., U.S. Office Action dated Nov. 1, 2024, directed to U.S. Appl. No. 17/180,573; 17 pages.

Fouts et al., U.S. Office Action dated Sep. 12, 2024, directed to U.S. Appl. No. 18/190,956; 20 pages.

Jansen, Mylène. (Sep. 15, 2017). "A Novel 3D joint space quantification method in patients with osteoarthritis in the knee." 64 pages.

Fouts et al., U.S. Advisory Action dated Oct. 18, 2024, directed to U.S. Appl. No. 16/785,367; 5 pages.

Agus et al. (2003). "A haptic model of a bone-cutting burr," Studies in Health Technology and Informatics 94: 4-10.

Alignment Disorders, Radiology Key, 2015, https://radiologykey.com/alignment-disorders/.

Allen, D. et al., Prevalence of associated deformities and hip pain in patients with cam-type femoroacetabular impingement, J Bone Joint Surg, vol. 91-B. No. 5, May 2009, pp. 589-594.

Anderson, Lucas A. et al., Acetabular Carilage Delamination in Femoroacetabular Impingement: Risk Factors and Magnetic Resonance Imaging Diagnosis, J Bone Joint Surg Am, vol. 91, No., 2009, pp. 305-313.

Atlas of MSK Measurements: how to draw the alpha angle, Stanford MSK, http://xrayhead.com/measure/show_measurement.php?i=3, Publication Year 2012 1 page (2012).

Atlas of MSK Measurements: how to draw the femoral version, Stanford MSK, http://xrayhead.com/measure/show_measurement.php?i=5, Publication Year 2012 1 page (2012).

Audenaert et al. (May 2012). "Imageless versus image-based registration in navigated arthroscopy of the hip," The Journal of Bone & Joint Surgery 94-B(5) 624-629.

Audenaert, Emmanuel A. et al., Development of a three-dimensional detection method of cam deformities in femoroacetabular impingement, Skeletal Radiology, vol. 40, 2011, pp. 921-927.

Audenaert, Emmanuel A. et al., Three-Dimensional Assessment of Cam Engagement in Femoroacetabular impingement, Arthroscopy, vol. 27, No. 2, 2011, pp. 167-171.

Beaule, Paul E. et al., Three-dimensional computed tomography of the hip in the assessment of femoroacetabular impingement, J Orthop Res, vol. 23, 2005, pp. 1286-1292.

Beck, M. et al., Hip morphology influences the pattern of damage to the acetabular cartilage: femoroacetabular impingement as a cause of early opsteoarthritis of the hip, J Bone Joint Surg, vol. 87-B, 2005, pp. 1012-1018.

Bei, Yanhong et al., Multibody dynamic simulation of knee contact mechanics, Med Eng Phys., vol. 26, No. 9, Nov. 2004, pp. 777-789.

Bouma, Heinse W. et al., Can Combining Femoral and Acetabular Morphology Parameters Improve the Characterization of Femoroacetabular Impingement?, Clin Orthop Rel Res, vol. 473, No. 4, 2015, pp. 1396-1403.

Broughton, N. S. et al., Reliability of radiological measurements in the assessment of the child's hip, J Bone Joint Surg, vol. 71-B, No. 1, 1989, p. 6-8.

Butler, Mark H., Current Technologies for Device Independence, Hewlett Packard, 2001, pp. 1-28.

Cadet, Edwin R. et al., Inter- and intra-observer agreement of femoroacetabular impingement (FAI) parameters comparing plain radiographs and advanced, 3D computed tomographic (CT)-generated hip models in a surgical patient cohort, Knee Surg Sports Traumatol Arthrosc, vol. 27, No. 7, 2014, pp. 2324-2331.

Carlisle, John C. et al., Reliability of Various Observers in Determining Common Radiographic Parameters of Adult Hip Structural Anatomy, The Iowa Orthopaedic Journal, vol. 31, 2011, pp. 52-58.

Chadayammuri, Vivek et al., Measurement of lateral acetabular coverage: a comparison between CT and plain radiography, J Hip Preservation Surgery, vol. 2, No. 4, Oct. 22, 2015, pp. 392-400.

Chadayammuri, Vivek et al., Passive Hip Range of Motion Predicts Femoral Torsion and Acetabular Version, J Bone Joint Surg Am., vol. 98, 2016, pp. 127-134.

Chavhan, Govind B. et al., Principles, Techniques, and Applications of T2-based MR Imaging and Its Special Applications, RadioGraphics, vol. 29, 2009, pp. 1433-1449.

Cheng, Hui et al., Comparison of 2.5D and 3D Quantification of Femoral Head Coverage in Normal Control Subjects and Patients with Hip Dyplasia, PLOS One, vol. 10, No. 11, Nov. 24, 2015, pp. 1-14.

Clohisy, John C. et al., A Systematic Approach to the Plain Radiographic Evaluation of the Young Adult Hip, J Bone Joint Surg Am., vol. 90, Supp. 4, 2008, pp. 47-66.

Clohisy, John C. et al., Radiographic Evaluation of the Hip has Limited Reliability, Clin Orthop Relat Res, vol. 467, 2009, pp. 666-675.

Clohisy, John C. et al., The Frog-leg Lateral Radiograph Accurately Visualized Hip Cam Impingement Abnormalities, Clin Orthop Relat Res, No. 462, Sep. 2007, pp. 115-121.

Cobb et al. (Apr. 30, 2010). "Cams and Pincer Impingement Are Distinct, Not Mixed," Clinical Orthopaedics and Related Research 468(8): 2143-2151.

Dandachli, W. et al., Analysis of cover of the femoral head in normal and dysplastic hips, J Bone Joint Surg, vol. 90-B, No. 11, 2008, pp. 1428-1434.

Dandachli, W. et al., Three-dimensional CT analysis to determine acetabular retroversion and the implications for the management of femoro-acetabular impingement, J Bone Joint Surg. vol. 91-B, No. 8, 2009, pp. 1031-1036.

Danz, J.C. et al., Three-dimensional portable document format: A simple way to present 3-dimensional data in an electronic publication, American Journal of Orthodontics and Dentofacial Orthopedics, vol. 140, No. 2, Aug. 2011, pp. 274-276.

Decision of Rejection dated Sep. 1, 2022, directed to CN Application No. 201780083846.8; 14 pages.

Dyonics Plan Hip Impingement Planning System: User Manual and Frequently Asked Questions, Smith & Nephew, Inc., 2014.

Eguizabal, Alma et al., A Weighting Strategy for Active Shape Models, IEEE International Conference on Image Processing, 2017.

Eijer, H. et al., Evaluation and Treatment of Young Adults with Femoro-Acetabular Impingement Secondary to Perthes' Disease, Hip Int., vol. 16, No. 4, 2006, pp. 273-280.

(56) References Cited

OTHER PUBLICATIONS

EOS Imaging. "EOS System," located at https://www.eos-imaging.com/us/our-expertise/imaging-solutions/eos-system, visited on Oct. 29, 2019. 8 pages.
Extended European Search Report dated May 13, 2020, directed to EP Application No. 17870894.7; 12 pages.
Fa, Lianggluo et al., Superiority of the modified Tonnis angle over the Tonnis angle in the radiographic diagnosis of acetabuular dysplasia, Experimental and Therapeutic Medicine, vol. 8, 2014, pp. 1934-1938.
Fabricant, Peter D. et al., Clinical Outcomes After Arthroscopic Psoas Lengthening: The Effect of Femoral Version, Arthroscopy, vol. 28, No. 7, 2012, pp. 965-971.
Fabricant, Peter D. et al., The Effect of Femoral and Acetabular Version on Clinical Outcomes After Arthroscopic Femoroacetabular Impingement Surgery, J Bone Joint Surg, vol. 97, No. 7, 2015, pp. 537-543.
First Office Action dated Aug. 31, 2021, directed to CN Application No. 201780083846.8; 25 pages.
Fouts et al., U.S. Election of Species Requirement dated Jun. 4, 2024, directed to U.S. Appl. No. 17/180,573; 6 pages.
Fouts et al., U.S. Notice of Allowance and Fee(s) Due mailed Nov. 3, 2022, directed to U.S. Appl. No. 17/143,091; 9 pages.
Fouts et al., U.S. Notice of Allowance and Fee(s) Due mailed Oct. 8, 2020, directed to U.S. Appl. No. 15/818,394; 7 pages.
Fouts et al., U.S. Office Action dated Apr. 21, 2020, directed to U.S. Appl. No. 15/818,394; 33 pages.
Fouts et al., U.S. Office Action dated Apr. 25, 2024, directed to U.S. Appl. No. 18/190,956; 32 pages.
Fouts et al., U.S. Office Action dated Dec. 20, 2019, directed to U.S. Appl. No. 15/818,394: 28 pages.
Fouts et al., U.S. Office Action dated Dec. 8, 2023, directed to U.S. Appl. No. 16/785,367; 39 pages.
Fouts et al., U.S. Office Action dated Feb. 15, 2019, directed to U.S. Appl. No. 15/818,394; 21 pages.
Fouts et al., U.S. Office Action dated Jun. 3, 2024, directed to U.S. Appl. No. 16/785,367; 43 pages.
Fouts et al., U.S. Office Action dated Mar. 1, 2022, directed to U.S. Appl. No. 16/785,367; 31 pages.
Fouts et al., U.S. Office Action dated Mar. 23, 2023, directed to U.S. Appl. No. 16/785,367; 18 pages.
Fouts et al., U.S. Office Action dated Nov. 9, 2023, directed to U.S. Appl. No. 18/190,956; 18 pages.
Fouts et al., U.S. Office Action dated Sep. 23, 2022, directed to U.S. Appl. No. 16/785,367; 21 pages.
Gosvig, K. K. et al., A new radiological index for assessing asphericity of the femoral head in cam impingement, J Bone Joint Surg, vol. 89-B, No. 10, Oct. 2007, pp. 1309-1316.
Hanson, Joey A. et al., Discrepancies in measuring acetabular coverage: revisiting the anterior and lateral center edge angels, Journal of Hip Preservation Surgery, vol. 2, No. 3, 2015, pp. 280-286.
Hellman, Michael D. et al., Radiographic Comparison of Anterior Acetabular Rim Morphology Between Pincer Femoroacetabular Impingement and Control, Arthroscopy, vol. 32, No. 3, 2016, pp. 468-472.
Hernandez, Ramiro J. et al., CT Determination of Femoral Torsion, AJR, vol. 137, Jul. 1981, pp. 97-101.
Hetsroni, Iftach et al., Anterior Inferior Illiac Spine Morphology Correlates With Hip Range of Motion: A Classification System and Dtynamic Model, Clin Orthop Relat Res, vol. 471, No. 8, Aug. 2013, pp. 2497-2503.
Heyworth, Benton E. et al., Preoperative Three-dimensional CT Predicts Intraoperative Findings in Hip Arthroscopy, Clin Orthop Rlat Res, vol. 470, No. 7, Jul. 2012, pp. 1950-1957.
International Preliminary Report on Patentability dated Aug. 23, 2022, directed to International Application No. PCT/US2021/018911; 10 pages.
International Preliminary Report on Patentability dated Jun. 13, 2023, directed to International Application No. PCT/US2021/072917; 9 pages.
International Preliminary Report on Patentability mailed on May 31, 2019 for PCT Application No. PCT/US2017/062603 filed Nov. 20, 2017, 11 pages.
International Search Report and Written Opinion mailed Jun. 1, 2021, directed to International Application No. PCT/US2021/018911; 17 pages.
International Search Report and Written Opinion mailed May 10, 2022, directed to International Application No. PCT/US2021/072917; 13 pages.
International Search Report and Written Opinion mailed on Feb. 1, 2018 for PCT Application No. PCT/US2017/062603 filed Nov. 20, 2017, 12 pages.
Ito, K. et al., Femoroacetabular impingement and the cam-effect: a MRI-based quantitative anatomical study of the femoral head-neck offset, J Bone Joint Surg, vol. 83-B, No. 2, Mar. 2001, pp. 171-176.
Jesse, Mary Kristen et al., Normal Anatomy and Imaging of the Hip: Emphasis on Impingement Assessment, Seminars in Musculoskeletal Radiology, vol. 17, No. 3, 2013, pp. 229-247.
Johnston, Todd L. et al., Relationship Between Offset Angle Alpha and Hip Chondral Injury in Femoroacetabular Impingement, Arthoroscopy, vol. 24, No. 6, 2008, pp. 669-675.
Kasten et al. (Apr. 2020). "End-To-End Convultional Neural Network for 3D Reconstruction of Knee Bones from Bi-Planar X-Ray Images," 12 pages.
Kelkar, Rajeev, Normal and Abnormal Mechanics of the Shoulder: Studies of Articular Geometry, Contact, and Kinematics, ProQuest Dissertations and Theses, 1996.
Kelly, Bryan T. et al., Alterations in Internal Rotation and Alpha Angles Are Associated With Arthroscopic Cam Decompression in the Hip, The American Journal of Sports Medicine, 2012, pp. 1-6.
Konishi, N. et al., Determination of acetabular coverage of the femoral head with use of a single anteroposterior radiograph. A new computerized technique, J Bone Joint Surg Am, vol. 75-A, No. 9, 1993, pp. 1318-1333.
Kraeutler, Matthew J. et al., Femoral Version Abnormalities Significantly Outweigh Effect of Cam Impingement on Hip Internal Rotation, J Bone Joint Surg Am., vol. 100-A, No. 3, 2018, pp. 205-210.
Krekel, P.R. et al., Interactive simulation and comparative visualisation of the bone-determined range of motion of the human shoulder, SimVis, 2006, pp. 1-13.
Laborie, Lene Bjerke et al., Radiographic measurements of hip dysplasia at skeletal maturity—new reference intervals baed on 2,036 19-yea-old Norwegians, Skeletal Radiol, vol. 42, No. 7, Jul. 2013, pp. 925-935.
Lambers et al., U.S. Advisory Action dated Oct. 21, 2021, directed to U.S. Appl. No. 16/261,464; 5 pages.
Lambers et al., U.S. Notice of Allowance and Fee(s) Due mailed May 13, 2022, directed to U.S. Appl. No. 16/261,464; 5 pages.
Lambers et al., U.S. Notice of Allowance and Fee(s) Due mailed Nov. 24, 2023, directed to U.S. Appl. No. 18/045,449; 6 pages.
Lambers et al., U.S. Office Action dated Dec. 15, 2020 directed U.S. Appl. No. 16/261,464; 16 pages.
Lambers et al., U.S. Office Action dated Dec. 20, 2021, directed to U.S. Appl. No. 16/261,464; 15 pages.
Lambers et al., U.S. Office Action dated Jul. 7, 2023, directed to U.S. Appl. No. 18/045,449; 14 pages.
Lambers et al., U.S. Office Action dated Jun. 11, 2021, directed to U.S. Appl. No. 16/261,464; 13 pages.
Larson, Christopher M. et al., Are Normal Hips Being Labeled as Pathologic? A CT-based Method for Defining Normal Acetabular Coverage, Clin Orthop Relat Res, vol. 473, No. 4, Apr. 5, 2015. pp. 1247-1254.
Larson, Christopher M. et al., Arthroscopic Hip Revision Surgery for Residual Femoroacetabular Impingement (FAI): Surgical Outcomes Compared With a Matched Cohort After Primary Arthroscopic FAI Correction, The Am J of Sports Med. vol. 42, No. 8, 2014, pp. 1785-1790.
Leboeuf, Fabien, Using LATEX to produce multi-media clinical reports, The PracTeX Journal, No. 1, 2011, pp. 1-14.

(56) References Cited

OTHER PUBLICATIONS

Lequesne, M. et al., The normal hip joint space: variations in width, shape, and architecture on 223 pelvic radiographs, Ann Rheum Dis, vol. 63, 2004, pp. 1145-1151.

Levy, David M. et al., Prevalence of Cam Morphology in Females with Femoroacetabular Impingement, Front. Surg., vol. 2, No. 61, Dec. 2015, pp. 1-5.

Linder et al. (Aug. 2013). "Fully Automatic Segmentation of the Proximal Femur Using Random Forest Regression Voting," IEEE Transactions on Medical Imaging 32(8):1462-1472.

Mardones, Rodrigo M. et al., Surgical Correction of "Cam-Type" Femoroacetabular Impingement: A Cadaveric Comparison of Open Versus Arthroscopic Debridement, Arthroscopy, vol. 25, No. 2, 2009, pp. 175-182.

Mardones, Rodrigo M. et al., Surgical Treatment of Femoroacetabular Impingement: Evaluation of the Effect of the Size of the Resection, J Bone Joint Surg Am, vol. 88A, Supp. 1, Mar. 2006, pp. 84-91.

Matsuda et al., Acute Iatrogenic Dislocation Following Hip Impingement Arthroscopic Surgery, Arthroscopy, vol. 25, No. 4, 2009, pp. 400-404.

Matsuda et al., Closed Intramedullary Derotational Osteotomy and Hip Arthroscopy for Cam Femoroacetabular Impingement From Femoral Retroversion, Arthroscopy Techniques, vol. 3, No. 1, 2014, pp. e83-e88.

McCarthy, Joseph et al., Anatomy, pathologic features, and treatment of acetabular labral tears, Clin Orthop Relat Res, No. 406, 2003, pp. 38-47.

Meyer, Dominik C. et al., Comparison of Six Radiographic Projections to Assess Femoral Head/Neck Ashpericity, Clin Orthop Relat Res. No. 445, 2006, pp. 181-185.

Milone, Michael T. et al., Novel CT-based Three-dimensional Software Improves the Characterization of Cam Morphology, Clin Orthop Relat Res, vol. 471, No. 8, Aug. 2013, pp. 2484-2491.

Minciullo et al. "Fully Automated Shape Analysis for Detection of Osteoarthritis from Lateral Knee Radiographs," 2016 23rd International Conference on Pattern Recognition (ICPR), Dec. 4-8, 2016, Cancún Center, Cancún, México; pp. 3787-3791.

Miyasaka, Dai et al., Three-dimensional Assessment of Femoral Head Coverage in Normal and Dysplastic Hips: A Novel Method, Acta Med., vol. 68, No. 5, 2014, pp. 277-284.

Murphy, S.B. et al., The prognosis in untreated dysplasia of the hip: A study of radiographic factors that predict the outcome, J Bone Joint Surg Am, vol. 77-A, No. 7, 1995, pp. 985-989.

Nepple, Jeffrey J. et al., Clinical and Radiographic Predictors of Intra-articular Hip Disease in Arthroscopy, Am J Sports Med, vol. 39, No. 2, 2011, pp. 296-303.

Nepple, Jeffrey J. et al., Diagnostic Imaging of Femoroacetabular Impingement, J Am Acad Orthop Surg, vol. 21, Suppl. 1, 2013, pp. S20-S26.

Nepple, Jeffrey J. et al., Do Plain Radiographs Correlate With CT for Imaging of Cam-type Femoroacetabular Impingement?. Clin Orthop Relat Res, vol. 470, No. 12, Dec. 2012, pp. 3313-3320.

Notzli, H.P. et al., The contour of the femoral head-neck junction as a predictor for the risk of anterior impingement, J Bone Joint Surg, vol. 84-B, 2002, pp. 556-560.

Office Action dated Aug. 23, 2023, directed to EP Application No. 17 870 894.7; 6 pages.

Ogata, S. et al., Acetabular cover in congenital dislocation of the hip, J Bone Joint Surg, vol. 72-B, No. 2, 1990, pp. 190-196.

Omeroglu, Hakan et al., Analysis of a radiographic assessment method of acetabular cover in developmental dysplasia of the hip, Arch Orthop Trauma Surg, vol. 122, No. 6, 2002, pp. 334-337.

Omeroglu, Hakan et al., Measurement of center-edge angle in developmental dysplasia of the hip: a comparison of two methods in patients under 20 years of age, Skeletal Radiol, vol. 31, No. 1, 2002, pp. 25-29.

Outerbridge, R.E., The etiology of chondromalacia patellae, J Bone Joint Surg, vol. 43-B, No. 4, 1961, pp. 556-560.

Ozcelik, Abdurrahman et al., Definition of a quantitative measurement method for acetabular version in a plain radiograph in the healthy adult hip, Eklem Hastalik Cerrahisi, vol. 26, No. 1, 2015, pp. 2-5.

Panoramic Fluoro, Radlink Inc., 2017, http:--www.radlink.com-index.php-products-software-surgeons-checklist-software-panoramic-fluoro-.

Perreira, Aimee C. et al., Multilevel Measurement of Acetabular Version Using 3-D CT-generated Models, Clin Orthop Relat Res, vol. 469, No. 2, Feb. 2011, pp. 552-561.

Phelps, A. et al., Embedding 3D Radiology Models in Portable Document Format, American Journal of Roentgenology, vol. 199, No. 6, Dec. 2012, pp. 1342-1344.

Rakhra, Kawan S. et al., Comparison of MRI Alpha Angle Measurement Planes in Femoroacetabular Impingement, Clin Orthop Relat Res, vol. 467, No. 3, 2009, pp. 660-665.

Reikeras, Olav et al., Cross table lateral radiography for measurement of acetabular cup version, Ann Transl Med., vol. 4, No. 9, 2016, pp. 1-4.

Reynolds, D. et al., Retroversion of the acetabulum: a cause of hip pain, J Bone Joint Surg, vol. 81-B, No. 2, Mar. 1999, pp. 281-288.

Ross, James R. et al., Intraoperative Fluoroscopic Imaging to Treat Cam Deformities: Correlation With 3-Dimensional Computed Tomography, Am J. Sports Med. vol. 42, No. 6, 2014, pp. 1370-1376.

Ruthensteiner, B. et al., Embedding 3D Models of Biological Specimens in PDF Publications, Microscopy Research and Technique, vol. 71, No. 11, 2008, pp. 778-786.

Schumann et al. (2013). "An Integrated System for 3D Hip Joint Reconstruction from 2D X-rays: A Preliminary Validation Study," Annals of Biomedical Engineering, 41(10): 2077-2087.

Second Office Action dated Mar. 16, 2022, directed to CN Application No. 201780083846.8; 17 pages.

Siebenrock, K.A. et al., Effect of Pelvic Tilt on Acetabular Retroversion: A Study of Pelves From Cadavers, Clin Orthop Relat Res. No. 407, Feb. 2003, pp. 241-248.

Stahelin, Lisca et al., Arthroscopic Offset Restoration in Femoroacetabular Cam Impingement: Accuracy and Early Clinical Outcome, Arthroscopy: The J of the Arthroscopic and Rel Surg, vol. 24, No. 1, 2008, pp. 51-57.

Stelzeneder, David et al., Can Radiographic Morphometric Parameters for the Hip Be Assessed on MRI?, Clin Orthop Relat Res, vol. 471, No. 3, Mar. 2013, pp. 989-999.

Stubbs, Allston J. et al., Classic measures of hip dysplasia do not correlate with three-dimensional computer tomographic measures and indices, Hip Int, vol. 21, No. 5, 2011, pp. 549-558.

Tannast, Moritz et al., Conventional radiographs to assess femoroacetabular impingement, Instr Course Lect, vol. 58, 2009, pp. 203-212.

Tannast, Moritz et al., Femoroacetabular Impingement: Radiographic Diagnosis—What the Radiologist Should Know, Am J Radiology, vol. 188, Jun. 2007, pp. 1540-1552.

Tannast, Moritz et al., Noninvasive Three-Dimensional Assessment of Femoroacetabular Impingement, J Orthop Res, vol. 25, No. 1, 2007, pp. 122-131.

Tannast, Moritz et al., Which Radiographic Hip Parameters Do Not Have to Be Corrected for Pelvic Rotation and Tilt?, Clin Orthop Relat Res, vol. 473, No. 4, Apr. 2015, pp. 1255-1266.

Tannenbaum, Eric et al., Gender and racial differences in focal and global acetabular version, J Arthroplasty, vol. 29, No. 2, Feb. 2014, pp. 373-376.

Tannenbaum, Eric P. et al., A Computed Tomography Study of Gender Differences in Acetabular Version and Morphology: Implications for Femoroacetabular Impingement, The J of Arthroscopic and Rel Surg, vol. 31, No. 7, 2015, pp. 1247-1254.

Thaler et al. "Volumetric Reconstruction from a Limited Number of Digitally Reconstructed Radiographs Using CNNs," Proceedings of a OAGM Workshop, 2018; pp. 13-19.

Tonnis, D et al., Acetabular and Femoral Anteversion: Relationship with Osteoarthritis of the Hip, J Bone Joint Surg Am, vol. 81-A, No. 12, 1999, pp. 1747-1770.

Tonnis, D., Congenital Dysplasia and Dislocation of the Hip in Children and Adults, Chapter 9, 1987, pp. 100-142.

(56) References Cited

OTHER PUBLICATIONS

Uchida, Soshi et al., Clinical and Radiographic Predicators for Worsened Clinical Outcomes After Hip Arthroscopic Labral Preservation and Capsular Closure in Developmental Dysplasia of the Hip, Am J Sports Med. Vol. 44, No. 1, 2016, pp. 28-38.

Van Bosse, Harold J. P. et al., Pelvic Positioning Creates Error in CT Acetabular Measurements, Clin Orthop Relat Res, vol. 469, No. 6, Jun. 2011, pp. 1683-1691.

Werner, Clement M. L. et al., Normal values of Wiberg's lateral center-edge angle and Lequesne's acetabular index—a coxometric update, Skeletal Radiol, vol. 41, 2012, pp. 1273-1278.

Wiberg, Gunnar, Studies on Dysplastic Acetabula and Congenital Subluxation of the Hip Joint with Special Reference to the Complication of Osteoarthritis, Orthopedic Clinic of Karolinska Institutet, 1939, pp. 1-39 and 129-135.

Wilson, J. D. et al., To what degree is digital imaging reliable? Validation of femoral neck shaft angle measurement in the era of picture archiving and communication systems, The British Journal of Radiology, vol. 84, Apr. 2011, pp. 375-379.

Zaltz, Ira et al., The Crossover Sign Overestimates Acetabular Retroversion, Clin Orthop Relat Res, vol. 471, 2013, pp. 2463-2470.

Zhao et al. "Automated Analysis of Femoral Artery Calcification Using Machine Learning Techniques," 2019 International Conference on Computational Science and Computational Intelligence (CSCI), Dec. 5-7, 2019, Las Vegas, Nevada, United States; pp. 584-589.

Ziegler, A. et al., Effectively incorporating selected multimedia content into medical publications, BMC Medicine, vol. 9, No. 17, 2011, pp. 1-6.

\* cited by examiner

SYSTEMS AND METHODS FOR GENERATING A THREE-DIMENSIONAL MODEL OF A JOINT FROM TWO-DIMENSIONAL IMAGES

CROSS-REFERENCE TO RELATED APPLICATIONS

This application claims the benefit of U.S. Provisional Application No. 63/125,932, filed Dec. 15, 2020, the entire contents of which are hereby incorporated by reference herein.

FIELD

This disclosure relates to orthopedics in general, and more particularly to methods and systems for imaging a joint.

BACKGROUND

Orthopedics is a medical specialty that focuses on the diagnosis, correction, prevention, and treatment of patients with skeletal conditions, including for example conditions or disorders of the bones, joints, muscles, ligaments, tendons, nerves and skin, which make up the musculoskeletal system. Joint injuries or conditions such as those of the hip joint or other joints can occur from overuse or over-stretching or due to other factors, including genetic factors that may cause deviations from "normal" joint morphology.

Joints are susceptible to a number of different pathologies (e.g., conditions or disorders, which may cause deviation from the normal joint morphology). These pathologies can have both congenital and injury-related origins. In some cases, the pathology can be substantial at the outset. In other cases, the pathology may be minor at the outset but, if left untreated, may worsen over time. More particularly, in many cases an existing pathology may be exacerbated, for example, by the dynamic nature of the joint, the substantial weight loads imposed on the joint, or a combination thereof. The pathology may, either initially or thereafter, significantly interfere with patient comfort and lifestyle and may require surgical treatment.

The current trend in orthopedic surgery is to treat joint pathologies using minimally-invasive techniques such as joint arthroscopy in which an endoscope is inserted into the joint through a small incision. Procedures performed arthroscopically include debridement of bony pathologies in which portions of bone in a joint that deviate from a "normal" or target morphology are removed. During a debridement procedure, the surgeon uses an endoscopic camera to view the debridement area, but because the resulting endoscopic image has a limited field of view and is somewhat distorted, the surgeon cannot view the entire pathology all at once. As a result, it is generally quite difficult for the surgeon to determine exactly how much bone should be removed, and whether the shape of the remaining bone has the desired geometry. Surgeons often use X-ray imaging to observe the perimeter of the bone in the region of the pathology to assess where and how much bone should be or has been removed, such as via an intraoperative C-arm imager. However, X-ray imaging can be limiting because only the horizon of the bone is observable in a given X-ray image and it can be difficult for the surgeon to compare what they are seeing in the arthroscopic imaging and in the X-ray imaging.

SUMMARY

According to an aspect, a three-dimensional model of at least a portion of a joint is generated from at least two two-dimensional images using a machine learning model trained on imaging data generated via a three-dimensional imaging modality. According to various aspects, the three dimensional model can be generated during a medical imaging session to model the state of the joint at the time of the imaging, enabling analysis of the joint closer-in-time to the imaging than generally available via three-dimensional imaging systems such as MRI. The two-dimensional imaging and three-dimensional model generation could be conducted, for example, near the beginning, during, and/or at the end of a medical procedure such that the three-dimensional model provides a snapshot of the joint in its current state at the time that may be most helpful to the practitioner. This could be useful, for example, during a surgical procedure on a joint for observing and/or measuring via the three-dimensional model where and how much bone to remove and/or where or how much bone has been removed based on the joint's current state.

According to an aspect, a method for modeling at least a portion of a joint before, during, and/or after a medical procedure includes receiving first imaging data capturing the at least a portion of the joint from a first imaging perspective and second imaging data capturing the at least a portion of the joint from a second imaging perspective that is different than the first imaging perspective, the first and second imaging data generated, e.g. intraoperatively, via a two-dimensional imaging modality, generating three-dimensional image data by back-projecting the first and second imaging data in three-dimensional space in accordance with a relative difference between the first and second imaging perspectives, generating a three-dimensional model of the at least a portion of the joint based on processing the three-dimensional image data with a machine learning model trained on imaging data generated via at least a three-dimensional imaging modality, and displaying a visualization based on the three-dimensional model of the at least a portion of the joint during the medical procedure.

Optionally, the two-dimensional imaging modality is C-arm fluoroscopy.

Optionally, the three-dimensional imaging modality is computed tomography or magnetic resonance imaging.

Optionally, generating the three-dimensional image data comprises aligning the first and second imaging data based on the relative difference between the first and second imaging perspectives.

Optionally, determining the relative difference between the first and second imaging perspectives is based on analyzing the first and second imaging data. The relative difference between the first and second imaging perspectives may be determined based on at least one fiducial captured in the first and second imaging data. The at least one fiducial may correspond to at least one object located within a field of view, and the relative difference between the first and second imaging perspectives is determined based on a predetermined geometry of the at least one object. Optionally, determining the relative difference between the first and second imaging perspectives may include identifying at least one feature of the at least a portion of the joint in the first and second imaging data and determining the relative difference between the first and second imaging perspectives based on a position of the at least one feature in the first imaging data and a position of the at least one feature in the second imaging data.

Optionally, processing the three-dimensional image data with a machine learning model may include generating multi-class voxels. Optionally, each multi-class voxel may represent bone or no-bone.

Optionally, the machine learning model may have been trained using training images generated via the two-dimensional imaging modality. The machine learning model may have been trained using multi-class voxel arrays that are based on training data generated via the three-dimensional imaging modality. The machine learning model may have been trained via the multi-class voxel arrays aligned to the training images generated via the two-dimensional imaging modality.

Optionally, the machine learning model may have been trained on two-dimensional image data generated from three-dimensional imaging modality imaging data.

Optionally, the method may include receiving third imaging data capturing the at least a portion of the joint from a third imaging perspective and generating the three-dimensional image data based on the first, second, and third imaging data.

Optionally, the visualization may include a rendering of at least a portion of the three-dimensional model.

Optionally, the visualization may include one or more measurements generated based on the three-dimensional model.

Optionally, the method may include removing bone during the medical procedure, wherein the three-dimensional model reflects removed bone. Alternatively, the method may exclude removing bone during the modeling.

Optionally, the visualization may include a representation of target bone removal.

Optionally, the representation of target bone removal may include at least one of a heat map and a contour map.

According to an aspect, a system includes one or more processor, memory, and one or more programs stored in the memory and configured for execution by the one or more processors for: receiving first imaging data capturing at least a portion of a joint from a first imaging perspective and second imaging data capturing the at least a portion of the joint from a second imaging perspective that is different than the first imaging perspective, the first and second imaging data generated, e.g. intraoperatively, via a two-dimensional imaging modality; generating three-dimensional image data by back-projecting the first and second imaging data in three-dimensional space in accordance with a relative difference between the first and second imaging perspectives; generating a three-dimensional model of the at least a portion of the joint based on processing the three-dimensional image data with a machine learning model trained on imaging data generated via at least a three-dimensional imaging modality; and displaying a visualization based on the three-dimensional model of the at least a portion of the joint during the medical procedure.

Optionally, the two-dimensional imaging modality is C-arm fluoroscopy.

Optionally, the three-dimensional imaging modality is computed tomography or magnetic resonance imaging.

Optionally, generating the three-dimensional image data includes aligning the first and second imaging data based on the relative difference between the first and second imaging perspectives. The one or more programs may include instructions for determining the relative difference between the first and second imaging perspectives based on analyzing the first and second imaging data. The relative difference between the first and second imaging perspectives may be determined based on at least one fiducial captured in the first and second imaging data. The at least one fiducial may correspond to at least one object located within a field of view, and the relative difference between the first and second imaging perspectives may be determined based on a predetermined geometry of the at least one object. Determining the relative difference between the first and second imaging perspectives may include identifying at least one feature of the at least a portion of the joint in the first and second imaging data and determining the relative difference between the first and second imaging perspectives based on a position of the at least one feature in the first imaging data and a position of the at least one feature in the second imaging data.

Optionally, processing the three-dimensional image data with a machine learning model comprises generating multi-class voxels.

Optionally, each multi-class voxel represents bone or no-bone.

Optionally, the machine learning model was trained using training images generated via the two-dimensional imaging modality.

Optionally, the machine learning model was trained using multi-class voxel arrays that are based on training data generated via the three-dimensional imaging modality.

Optionally, the machine learning model was trained via the multi-class voxel arrays aligned to the training images generated via the two-dimensional imaging modality.

Optionally, the machine learning model was trained on two-dimensional image data generated from three-dimensional imaging modality imaging data.

Optionally, the one or more programs include instructions for receiving third imaging data capturing the at least a portion of the joint from a third imaging perspective and generating the three-dimensional image data based on the first, second, and third imaging data.

Optionally, the visualization comprises a rendering of at least a portion of the three-dimensional model.

Optionally, the visualization comprises one or more measurements generated based on the three-dimensional model.

Optionally, the three-dimensional model reflects removed bone.

Optionally, the visualization includes a representation of target bone removal. The representation of target bone removal may include at least one of a heat map and a contour map.

According to an aspect, a non-transitory computer readable medium is provided storing one or more programs for execution by one or more processors of a computing system for performing any of the methods or any combination of the methods above. According to an aspect, a computer program product is provided comprising instructions which, when executed by one or more processors of a computer system, cause the computer system to perform any of the methods or any combination of the methods above.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which.

DETAILED DESCRIPTION

Figure 1:
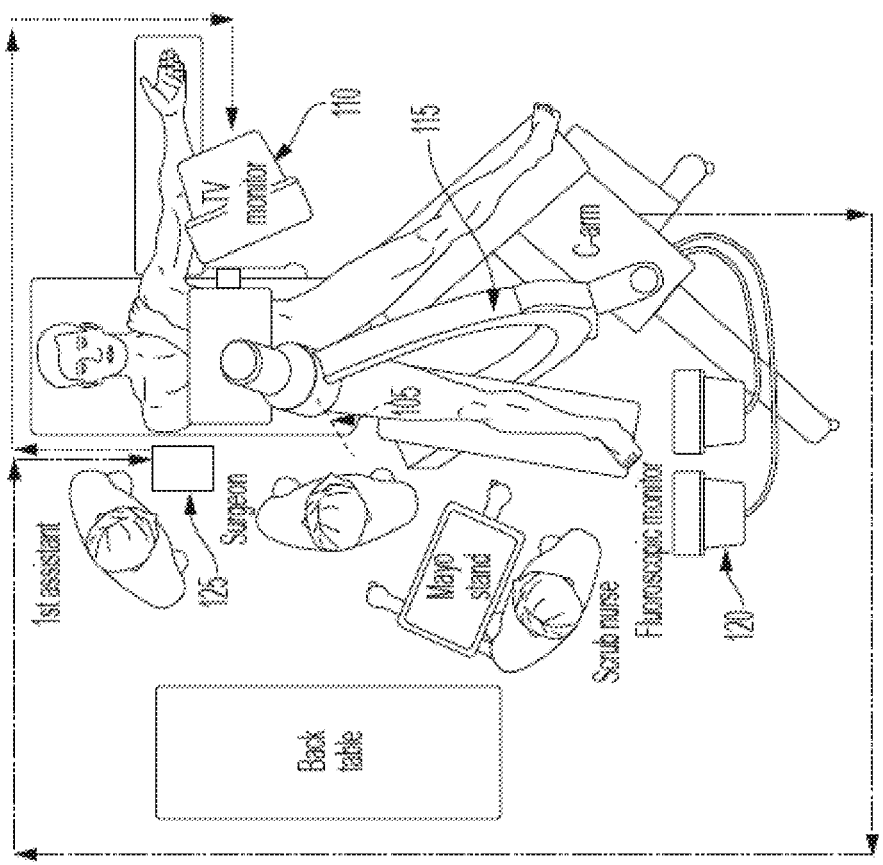
FIG. 1 illustrates an exemplary surgical suite incorporating an exemplary system for guiding a surgeon in removing bone from a portion of a joint during a surgical procedure.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Systems and methods, according to various aspects, include generating a three-dimensional model of anatomy of a subject from at least two two-dimensional images using a machine learning model trained on imaging data generated via a three-dimensional imaging modality. According to various aspects, two-dimensional images of anatomy of a patient from different perspectives are back-projected into three-dimensional space based on the relative difference in perspectives between the images to generate a set of multi-channel voxels. The set of multi-channel voxels are provided to a machine learning model that has been trained to transform multi-channel voxels into multi-class voxels. The set of multi-class voxels are then transformed into a meshed three-dimensional model, such as an STL file format. The three-dimensional model is then used to generate a visualization associated with the imaged anatomy, which can include a rendering of the three-dimensional model.

According to various aspects, the three dimensional model can be generated during, or immediately before or after, a medical imaging session to model the state of the anatomy of interest at the time of the imaging, enabling analysis of the anatomy closer-in-time to the image capture than generally available via three-dimensional imaging systems such as CT and MRI. The two-dimensional imaging and three-dimensional model generation could be conducted, for example, near the beginning, during, and/or at the end of a medical procedure such that the three-dimensional model provides a snapshot of the anatomy in its current state at the time that may be most helpful to the practitioner. This could be useful, for example, for a surgical procedure on a joint for observing and/or measuring via the three-dimensional model where and/or how to treat a joint, such as where and/or how much bone to remove and/or where or how much bone has been removed based on the joint's current state. According to various aspects, the three dimensional model can be generated and/or updated near the completion of a medical procedure such as for representing the final form of the anatomy resulting from the medical procedure. For example, a surgical procedure that includes removal of bone may include generating the three dimensional model and/or updating the three dimensional model after bone has been removed and determining from the model whether a sufficient amount of bone has been removed. If so, the surgery can end but, if not, the surgery can continue with further bone removal. In some examples, a model created at the end of the medical procedure could be added to the medical record. In some examples, a "before" model can be generated before or at the beginning of a medical procedure and an "after" model can be generated at or near the end of the procedure and the two models can be added to the medical record to document the procedure and/or can be displayed to a patient to help describe the procedure, which can improve patient engagement and satisfaction. According to various aspects, three-dimensional modeling according to the principles described herein can be used in support of various medical procedures, including non-surgical procedures, which can include pre-operative and/or post-operative imaging and planning sessions, or treatment procedures involving non-surgical intervention. According to various aspects, three-dimensional modeling according to the principles described herein can be used during surgical procedures, such as in support of removal of bone to treat femoroacetabular impingement, cutting the pelvis for a periacetabular osteotomy (PAO), preparing for a total knee arthroplasty (TKA), or placing pedicle screws in a spine.

According to various aspects, the three-dimensional model can be used for pre-procedural planning for a subsequent medical procedure, such as for planning where and how much bone to remove during a subsequent surgical procedure on a portion of a joint. Since two-dimensional imaging is typically more widely available and less expensive than three-dimensional imaging, the systems and methods described herein according to various aspects can expand the availability of three-dimensional visualization and/or analysis of a joint and/or provide three-dimensional modeling and/or analysis at reduced cost.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to devices or systems for performing the operations herein. The devices or systems may be specially constructed for the required purposes, may comprise a general purpose computer selectively activated or reconfigured by a computer program stored in the computer, or may include any combination thereof. Computer instructions for performing the operations herein can be stored in any combination of non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, or any type of media suitable for storing electronic instructions, and each coupled to a computer system bus. One or more instructions for performing the operations herein may be implemented in or executed by one or more Application Specific Integrated Circuits (ASICs), Field Programmable Gate Arrays (FPGAs), Digital Signal Processing units (DSPs), Graphics Processing Units (GPUs), or Central Processing Units (CPUs). Furthermore, the computers referred to herein may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Although the following examples often refer to a joint, such as a hip joint, hip joint pathologies, and hip joint characteristics and measurements, it is to be understood that systems, methods, techniques, visualizations, etc., it is within the scope of the invention to use the systems and methods for analyzing and visualizing other anatomical regions of a patient, including other joints, such as knee joints, shoulder joints, elbow joints, vertebral joints, ankle joints, etc., and other bones, such as the cranium, vertebra, femur, pelvis, etc.

FIG. 1 illustrates an exemplary surgical suite incorporating an example of a system for guiding a surgeon in treating bone during a surgical procedure. In a typical arthroscopic surgical suite, the surgeon uses an arthroscope 105 and a display 110 to directly view an internal surgical site. In addition, the surgeon may also use a C-arm X-ray machine 115 and a fluoroscopic display 120 to image the internal surgical site. The surgical suite can include a computing system 125 that can generate a three-dimensional model from two-dimensional images, such as generated by a C-arm X-ray machine 115.

Computing system 125 can comprise one or more processors, memory, and one or more programs stored in the memory for causing the computing system to provide some or all of the functionality described herein. According to some examples, computing system 125 comprises a tablet device with an integrated computer processor and user input/output functionality, e.g., a touchscreen. The computing system 125 may be at least partially located in the sterile field, for example, the computing system 125 may comprise a touchscreen tablet mounted to the surgical table or to a boom-type tablet support. The computing system 125 may be covered by a sterile drape to maintain the surgeon's sterility as he or she operates the touchscreen tablet. The computing system 125 may comprise other general purpose computers with appropriate programming and input/output functionality, e.g., a desktop or laptop computer with a keyboard, mouse, touchscreen display, heads-up display, gesture recognition device, voice activation feature, pupil reading device, etc.

Figure 2:
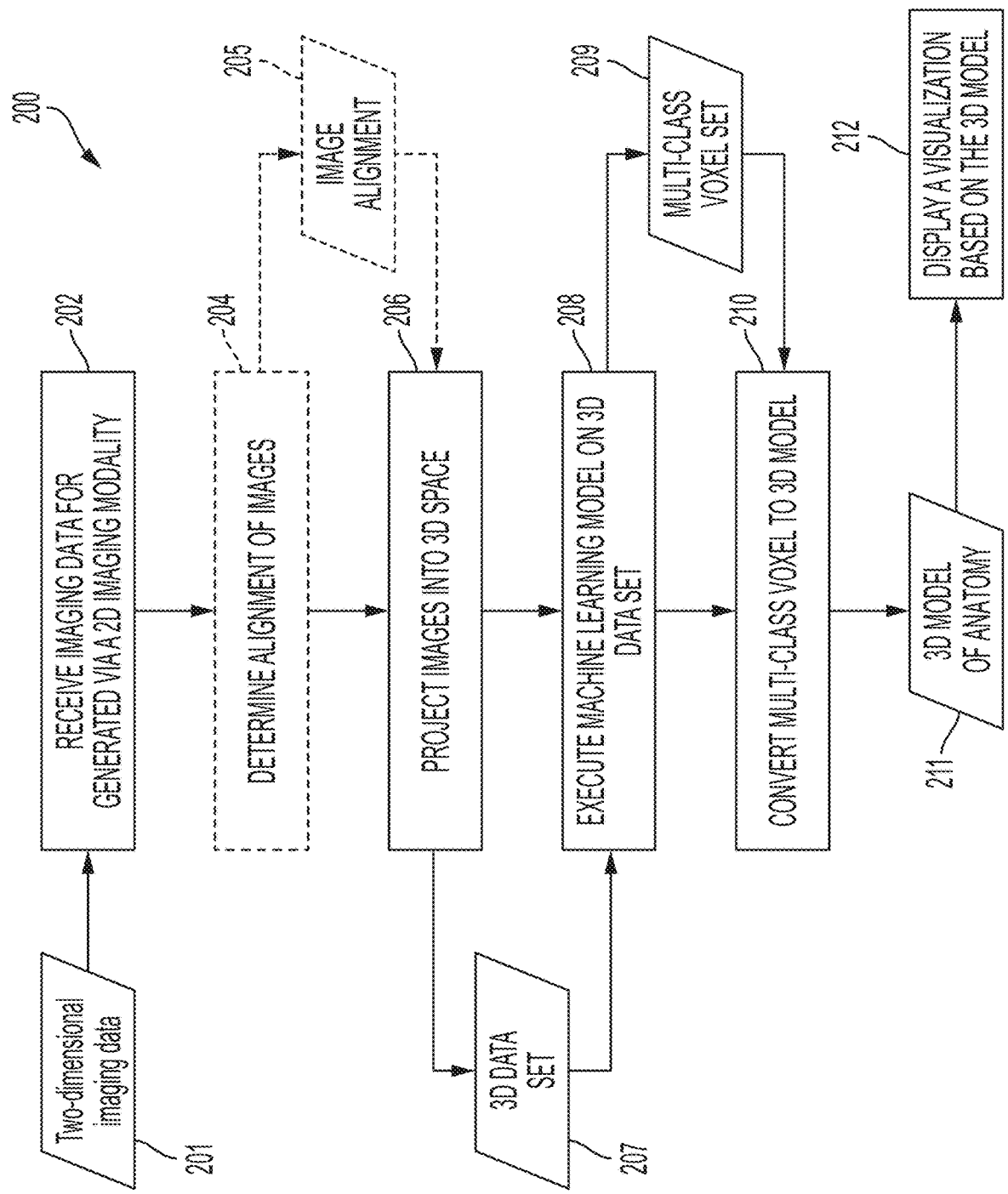
FIG. 2 is a block diagram of an exemplary method for generating a three-dimensional model from a plurality of two-dimensional images of a joint of a patient.

FIG. 2 is a block diagram of a method 200 for generating a three-dimensional model from a plurality of two-dimensional images of anatomy a patient, according to some examples. In some examples, the anatomy is a joint and the three-dimensional model generated is a three-dimensional model of a portion of the joint, which can include one or more bones of the joint. Method 200 can be used in support of a medical procedure, which can be a surgical or non-surgical procedure, to visualize aspects of patient anatomy. Method 200, in its entirety or portions of method 200, can be performed before, during, and/or after a medical procedure. In some examples, the medical procedure includes non-surgical treatment of a joint of the patient. In some examples, the medical procedure is a surgical procedure. The surgical procedure may include surgical treatment of patient anatomy, which can include, for example, bone removal, bone cutting, mounting of hardware to or into bone, repositioning of bone, etc. Examples of surgical treatment of bone are cutting the pelvis for a periacetabular osteotomy (PAO), preparing for a total knee arthroplasty (TKA), and placing pedicle screws in a spine.

At step 202, imaging data 201 associated with anatomy of interest of a patient that was generated via a two-dimensional imaging modality is received at a computing system, such as computing system 125 of FIG. 1. The anatomy of interest could include one or more bones, such as one or more bones of a joint. The following discussion often refers to the imaging of a joint, but it should be understood that the systems and methods described herein are not limited to joints and could be applied to any bony anatomy of a patient. Further, it will be understood to one of skill in the art that the principles describes herein can be extended to tissue other than bone (e.g., tendons, ligaments, muscles, organs) via the use of suitable imaging modalities. The imaging can capture multiple different bones or portions of multiple different bones, such as the head of a femur and a portion of the pelvis. In the example of trauma, the imaging can capture multiple bone fragments of a fractured bone. The imaging data can include two-dimensional images generated via a two-dimensional imaging modality, such as an X-ray imaging modality. For example, the two-dimensional images may be generated by C-arm X-ray machine 115 of FIG. 1. Any suitable X-ray system may be used, including an X-ray system capable of generating a sequence of images (often referred to as a fluoroscopy system) and an X-ray system designed to generate a single image (often referred to as a radiography system). The two-dimensional images may have been generated during an imaging session, including an outpatient imaging session or an inpatient imaging session. The imaging session may be associated with a surgical procedure and may be a pre-operative imaging session, an intra-operative imaging session, or a post-operative imaging session. According to various examples, the imaging session may be associated with a non-surgical treatment, such as associated with diagnostic procedure or other non-surgical treatment. According to various examples, method 200 includes generating the two-dimensional images.

Figure 3:
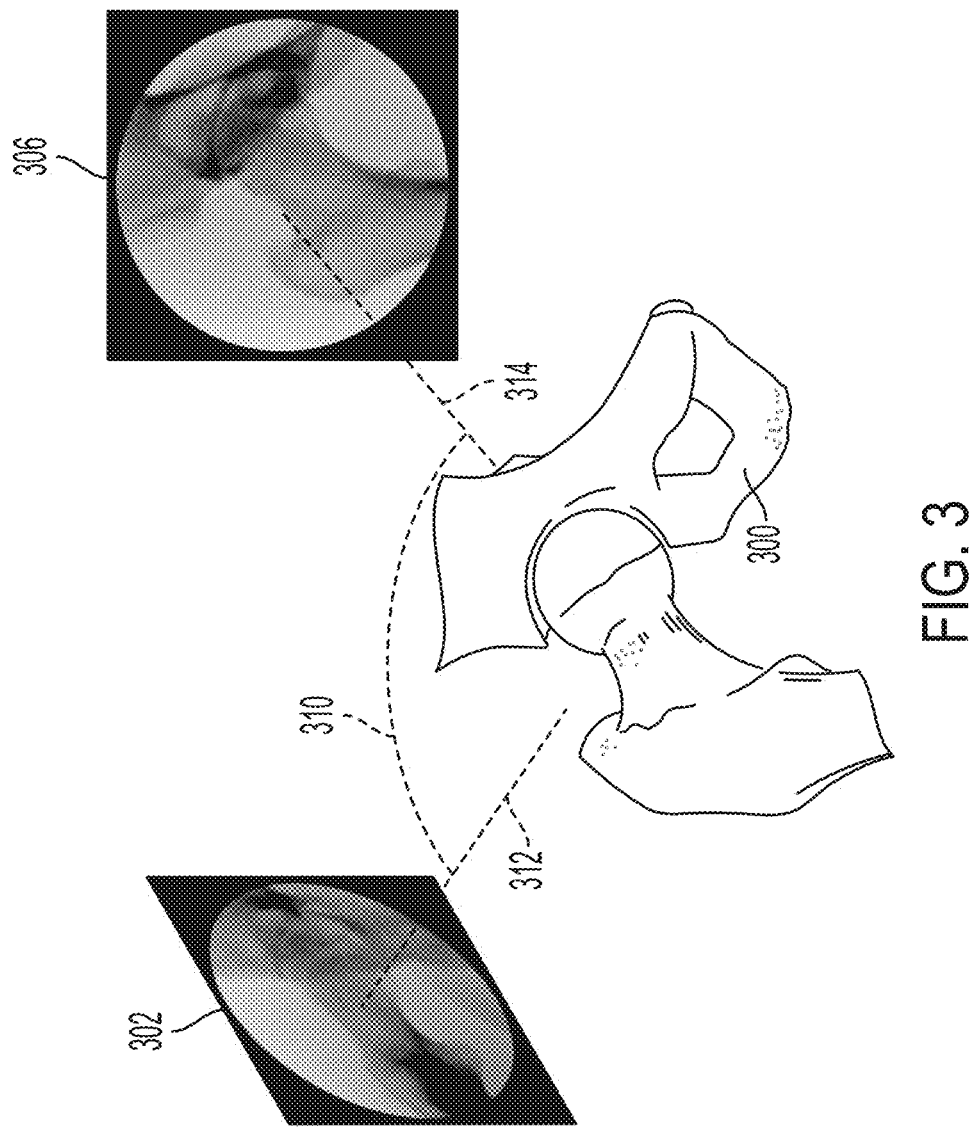
FIG. 3 illustrates exemplary two-dimensional X-ray images of a hip joint captured from two different imaging perspectives.

The imaging data includes two-dimensional imaging capturing anatomy of interest of the patient from at least two different perspectives relative to the anatomy. The imaging could capture, for example, joint of the patient or at least a portion of the joint from two different perspectives relative to the joint. For example, a first two-dimensional image may capture at least a portion of the patient's joint from a first imaging perspective and a second two-dimensional image may capture the joint or joint portion from a second imaging perspective that is different than the first imaging perspective. FIG. 3 illustrates two-dimensional X-ray images of a hip joint 300 captured from two different imaging perspectives. Image 302 captures the patient's hip joint 300 from a first perspective and image 306 captures the patient's hip joint 300 from a second perspective that is different than the first.

Figure 4B:
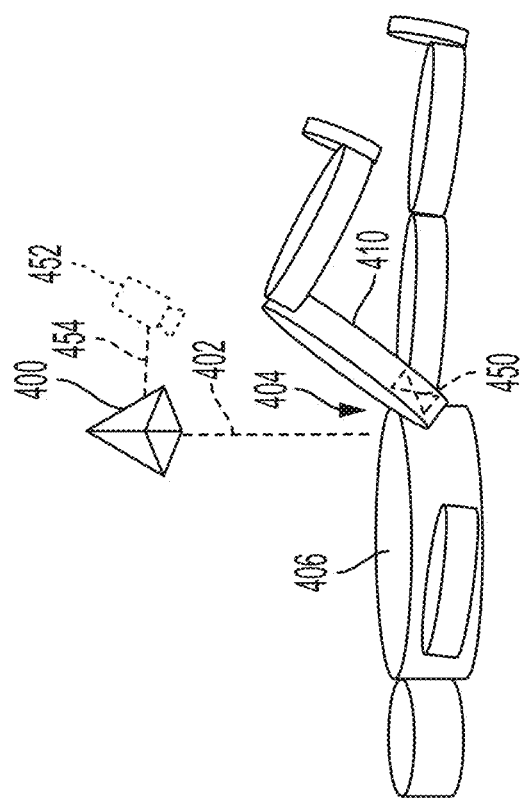
FIG. 4A and FIG. 4B illustrate examples of different ways of generating two-dimensional imaging data from different perspectives.
Figure 4A:
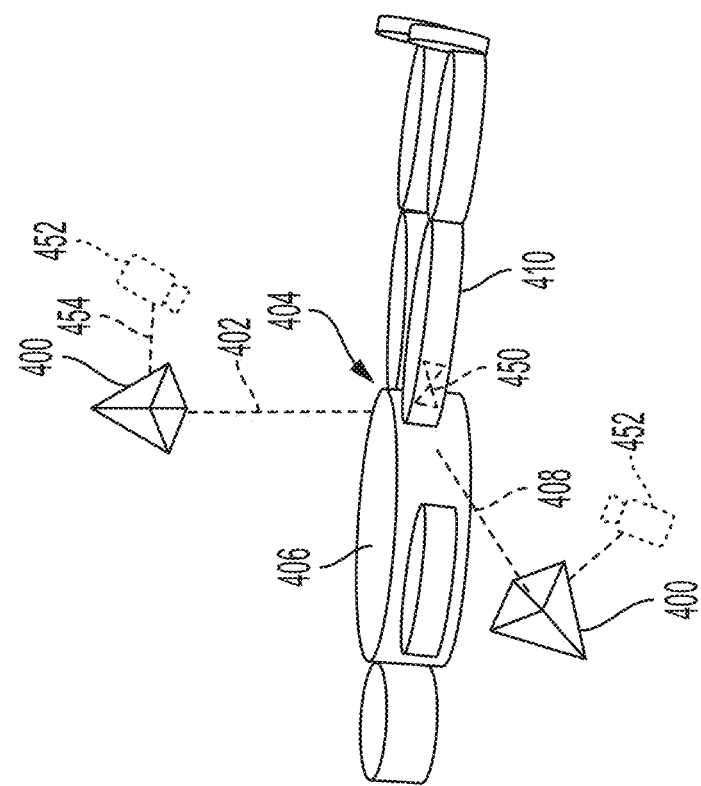

The different imaging perspectives can be achieved by moving the imager and/or by moving the patient. For example, in FIG. 4A, the imager 400 can move from a first position 402 for capturing a first perspective of the hip joint 404 of the patient 406 to a second position 408 for capturing a second perspective of the hip joint 404 of the patient 406. As illustrated in FIG. 4A, the first perspective can be, for example, an anterior-posterior perspective and the second perspective can be, for example, a lateral perspective. However, these perspectives are merely exemplary and it should be understood that any perspectives and combinations of perspectives can be used. The patient 406 may remain stationary while capturing the different perspectives of the joint or portion thereof or some or all of the patient may be moved between perspectives, such as to accommodate the imager and/or to move portions of the body out of or into the field of view. In some examples, the imager 400 remains stationary and at least a portion of the patient 406 is moved to capture images of different perspectives of the joint. For example, the imager 400 may remain in the first position 402 with the patient positioned as shown in FIG. 4A to obtain an image of the joint 404 from a first perspective and the patient's leg 410 may be abducted (e.g., into a frog-leg position) to the position illustrated in FIG. 4B to obtain a second image of the joint 404 from a second perspective.

The imaging data can include any number of images from any number of perspectives and need not be limited to two. For example, the imaging data may include three images from three perspectives, four images from four perspectives, five images from five perspectives, etc. According to some examples, images are generated with the joint positioned in standardized positions to capture standard perspectives of the joint. For example, in some examples, for a hip joint, the imager is positioned in an anterior-posterior position relative to the patient, and the patient's leg is positioned in one or more of the following standard positions for hip arthroscopy imaging: (1) 0° rotation and 0° flexion, (2) 30° internal rotation and 0° flexion, (3) 30° external rotation and 0° flexion, (4) 0° rotation and 50° flexion, (5) 40° external rotation and 50° flexion, (6) 60° rotation and 50° flexion.

Returning to FIG. 2, method 200 can include the optional step 204 of determining a relative difference between the first and second imaging perspectives. For example, with reference to FIG. 3, step 204 can include determining the angle 310 between the imaging axes 312 and 314. Step 204 can include determining the positions and imaging angles of the imager associated with the different images relative to one another or relative to a reference coordinate system.

Figure 5:
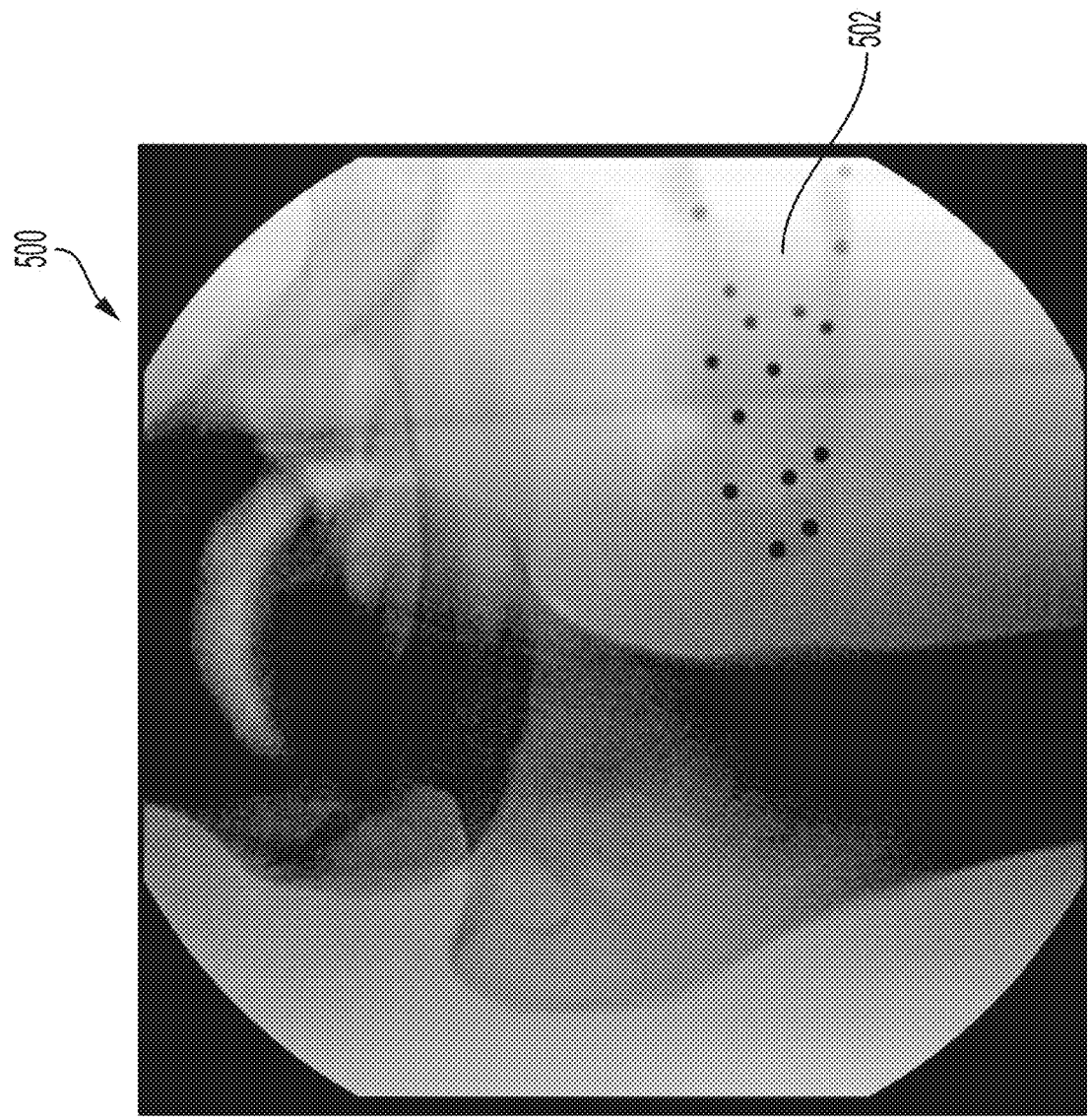
FIG. 5 illustrates an example of determining the relative perspectives of two-dimensional images using a radio-opaque fiducial located within the imaging field of view.

According to various examples, the relative difference between the imaging perspectives can be determined in step 204 via analysis of the images themselves. In some examples, a fiducial in the images can be used to determine the different perspectives based on the differences in appearance of the fiducial in the images. FIG. 5 illustrates one way of determining the relative perspectives of the two-dimensional images, which uses a fiducial located within the imaging field of view. In the illustrated example, the fiducial is a set of radio-opaque markers 502 that is visible in the X-ray image 500. The radio-opaque markers 502 may be disposed on an adhesive that can stick to the patient's skin. The set of radio-opaque markers 502 may be disposable. The set of radio-opaque markers 502 may be identified via any suitable image analysis technique, such as including any suitable edge detection technique. The size, shape, and position of the radio-opaque markers 502 in a given image can be compared to the known size and shape of the markers 502 to determine the perspective of the given image relative to a global reference or relative to another image.

According to various examples, a secondary imaging system can be used to determine the relative difference between the imaging perspectives of the two-dimensional images used for generating the three-dimensional model. The secondary imaging system can be, for example, an optical imaging system that may acquire images of the patient at or near the times that the two-dimensional images used for generating the three-dimensional model are generated. One or more fiducials used for determining the relative difference between the imaging perspectives may be captured in images generated by the secondary imaging system and the relative positions and orientations of the one or more fiducials in the secondary imaging system images can be used to determine the relative difference between the imaging perspectives of the two-dimensional images used for generating the three-dimensional model, such as based on a predetermined position and orientation of the secondary imaging system relative to the two-dimensional modality system. For example, with reference to FIG. 4A and FIG. 4B, a fiducial 450 may be positioned on the leg 410 of the patient 406, such as on the skin or on a device attached to the leg, and a secondary imaging system 452 may capture one or more images of the fiducial 450 at or near the same time that the imager 400 captures each two-dimensional image used for generating the three-dimensional model. The secondary imaging system 452 or a processing system (such as computing system 125 of FIG. 1) communicatively coupled to secondary imaging system 452 may analyze the secondary imaging system images to determine the change in position and orientation of the fiducial, such as due to change in position of the imager 400 (and secondary imaging system 452) as shown in FIG. 4A and/or change in position of the leg 410 of the patient 406 as shown in FIG. 4B. This change in position and orientation of the fiducial in the secondary imaging system images may be used along with the known position and orientation of the secondary imaging system 452 relative to the imager 400 (e.g., the secondary imaging system 452 may be rigidly connected to the imager 400 as indicated by line 454) to determine the relative difference between the imaging perspectives of the two-dimensional images used for generating the three-dimensional model.

The one or more fiducials 450 can be any feature identifiable in images generating by the secondary imaging system 452. For such identification purposes, pattern recognition capabilities can be provided by the secondary imaging system 452 or a computing system communicatively coupled to the secondary imaging system 452. One or more of the fiducials 450 may be active markings (e.g., emitting radiation to be detected by the secondary imaging system 452). Additionally, or in the alternative, one or more of the fiducials 450 may be passive markings. Passive markings may have reflecting or non-reflecting properties. Passive markings may be realized (e.g., by printing) on any rigid (e.g., planar) or flexible substrate attached to or implanted in the patient and/or painted on the patient's skin.

Figure 6:
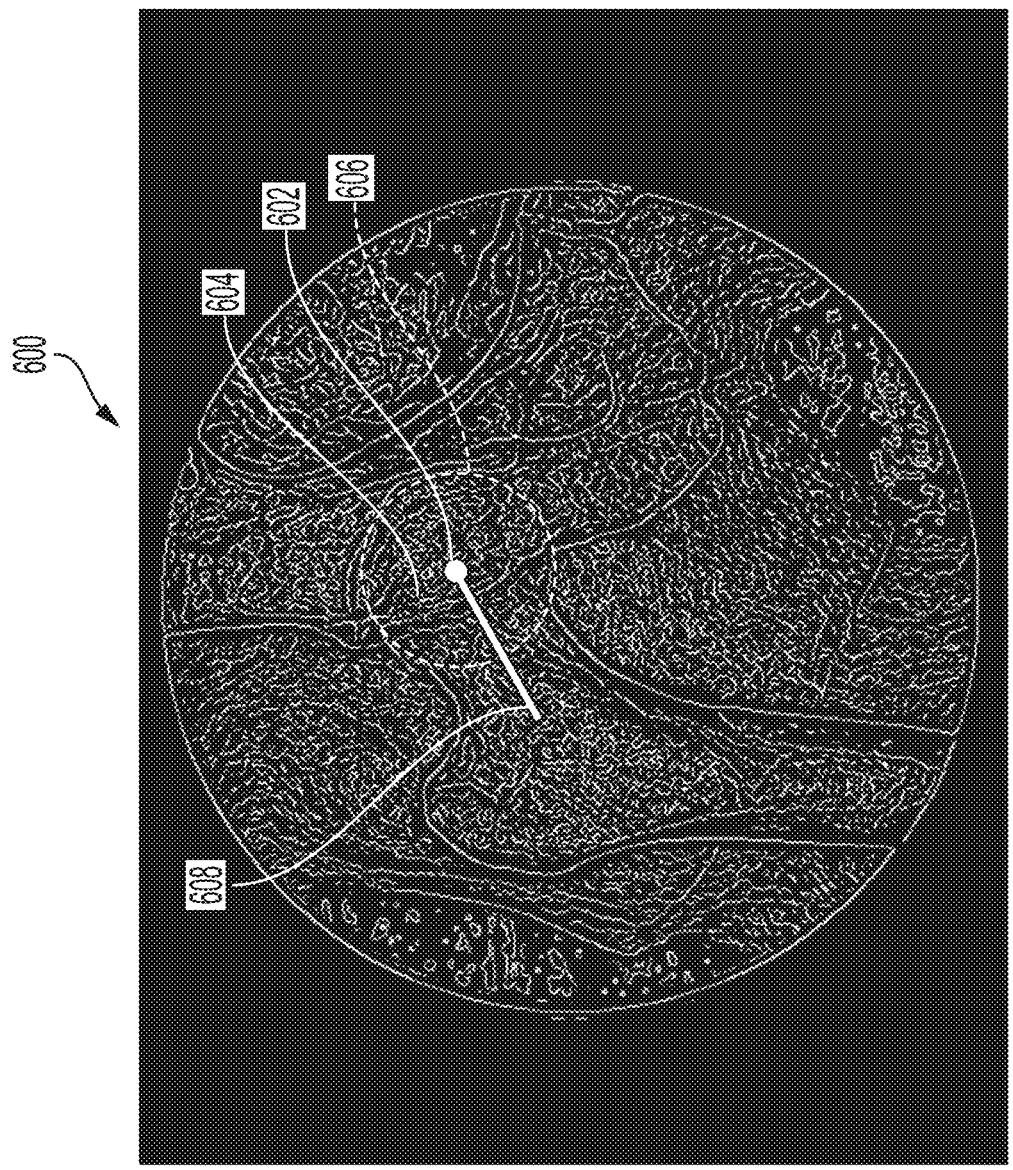
FIG. 6 illustrates an exemplary edge detection operation performed on a two-dimensional image to identify anatomy in the image for use in determining the relative perspectives of two-dimensional images.

An alternative or additional way of determining the different perspectives of the images based on analysis of the images includes identifying one or more features of the anatomy in the images and comparing the relative locations, sizes, shapes, etc., of those features to determine the relative perspectives. FIG. 6 illustrates an edge detection operation performed on a two-dimensional image to identify edges of at least a portion of the femur in the image, such as edges of the femoral head, the femoral neck, the greater trochanter, the lesser trochanter, and/or any other portions of the femur. According to various examples, any suitable edge detection technique may be used, including industry standard methods such as Sobel, Canny, and Scharr edge detection methods. In FIG. 6, the center 602 of the femoral head 604 may be detected by first detecting the perimeter 606 of the femoral head in the image 600, using any suitable technique, such as a Hough transform or machine learned models trained on images of similar anatomy. Once the femoral head is identified, the center of the femoral head in the x and y dimensions may be determined. In some examples, the mid-line 608 of the femoral neck is identified, such as by using edge detection techniques to identify edges near the femoral head and looking for the shortest distance between points on the superior portion of the neck and points on the inferior portion of the neck. According to various examples, the femoral neck and/or any other anatomical feature of interest can be identified using a machine learning algorithm, such as a convolutional neural network (CNN) or a region based CNN (R-CNN). The relative sizes, shapes, and positions of the various physiological features identified in the images can be compared to determine the relative perspectives associated with the images.

In some examples, the relative perspectives associated with different images in the imaging data can be determined in step 204 via information associated with a position of an imager. For example, an imaging system may have one or more sensors that track a position of the imager and may provide positional information with the associated image.

The result of optional step 204 is information 205 indicating the relative differences in perspectives of the images in the imaging data. The information 205 can include any of distances (e.g., focal distances) between an imager and the imaged anatomy, positions and/or angles relative to a fixed reference frame, angles between imaging axes, etc., for any images in the imaging data.

In some examples, the relative differences in the perspectives between different images are assumed rather than determined, such that step 204 does not need to be performed. For example, orthogonal perspectives may be assumed where the imager of the imaging system is repositioned between image captures by repositioning the imager ninety degrees between captures. In some examples, a practitioner operating the imaging system may be instructed to generate orthogonal image captures (or any other fixed perspective differences).

Returning to FIG. 2, method 200 continues to step 206 in which the two-dimensional images in the imaging data 201 are back-projected (since the term "projection" typically refers to transforming from a three-dimensions space to a two-dimensional space, "back-projection" is used here to refer to transforming from two-dimensional space to three-dimensional space) into three-dimensional space based on the relative differences in the perspectives of the images. The projection of the images into three-dimensional space takes into account the different perspectives of the images, which can be based on the perspective information 205 generated during step 204 or based on a predefined difference in perspective, such as orthogonality between image perspectives.

The projection of the images into three-dimensional space can include various transformations to account for the properties of the imaging system and/or distortions of the imaged anatomy captured in the images. For example, since X-rays do not travel in parallel lines but, rather, conically, an image is changed in scale as it is back-projected over the 3D volume. Other transformations may be used to account for skew, distortion, and/or perspective effects. The projection of the two-dimensional images into three-dimensional space does not alter the pixel values of the images, but rather, alters where the pixel values are located in each layer of the respective projection.

According to various examples, images can be trimmed or otherwise altered prior to projection. For example, each image may be cropped to a predefined dimension and/or predefined aspect ratio and/or pixel values may be normalized.

Figure 7A:
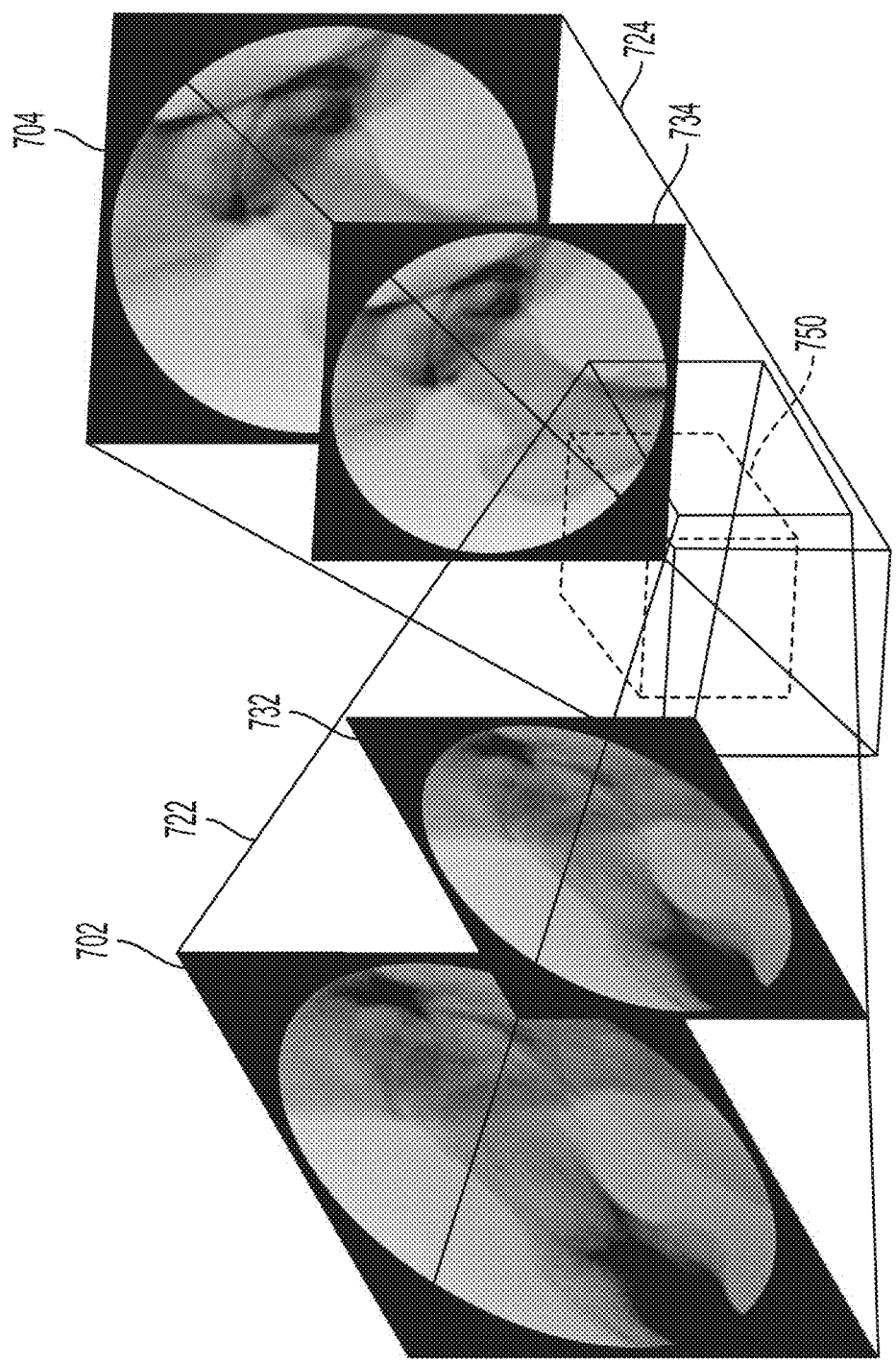
FIG. 7A illustrates an exemplary back-projection process used for transforming two-dimensional imaging data into three-dimensional data.

The back-projection of the images into three-dimensional space, according to various examples, is illustrated conceptually in FIG. 7A. The two-dimensional images 702, 704 are swept in the back-projection dimension. According to some examples, this sweeping may result in a respective "pyramid stump" 722, 724 in which pixel values of the images are replicated across the back-projection dimension based on the differences in perspectives of the images and various transformations discussed above. The pyramid stump shape may be appropriate, for example, when modeling an X-ray source generating the images 702, 704 as a pinhole camera. Other sweeping shapes may be used for other imaging modalities. Simplistic examples of a replication 732 for image 702 and a replication 734 for image 704 are provided in FIG. 7A to further illustrate the concept. The shape and position of each pyramid stump 722, 724 is based on the differences in perspectives of the images and various transformations discussed above.

According to various examples, a three-dimensional voxel grid 750 is placed in the region in which the pyramid stumps 722, 724 of the two images overlap. The voxel size of voxel grid 750 may be chosen to match the desired resolution of the three-dimensional model (e.g. 1 mm). The overall size of the voxel grid 750 can be any suitable size, and in some examples, may be selected based on the size of the area to be modeled (e.g. 128×128×128 at 1 mm voxel size for region corresponding to a cube with 128 mm edge length). The values of the voxels over this grid 750 are assigned by sampling the images 702, 704 at the location of the projection of the respective voxel center, yielding one value per input image (e.g. two values for each voxel when using two input images). Thus, each voxel has a value for a respective image that is determined from the pixel(s) of the image that are at the corresponding location in the image. A voxel could have the same value as a corresponding pixel, such as where a voxel directly maps to a single pixel, or could have a value that is a function of multiple pixel values, such as an average of surrounding pixel values. According to various examples, a pixel value could contribute to the values of multiple voxels, such as where voxel resolution is finer than pixel resolution.

The results of step 206 can be a set of voxels with each voxel having multiple values associated with it (one value for each of the two-dimensional images). For example, where the imaging data 201 includes two two-dimensional images, a voxel generated in step 206 has a first value (e.g., grayscale intensity value) that corresponds to the pixel value of the projection of the voxel center onto the first image, and an intensity value that corresponds to the pixel value of the projection of the voxel center onto the second image. In some examples, a voxel may have a single value that is a function of multiple images. For example, a voxel value could be an average of pixel values from images 702 and 704, such that each voxel has just a single value generated from the pixel values of both images.

Figure 7B:
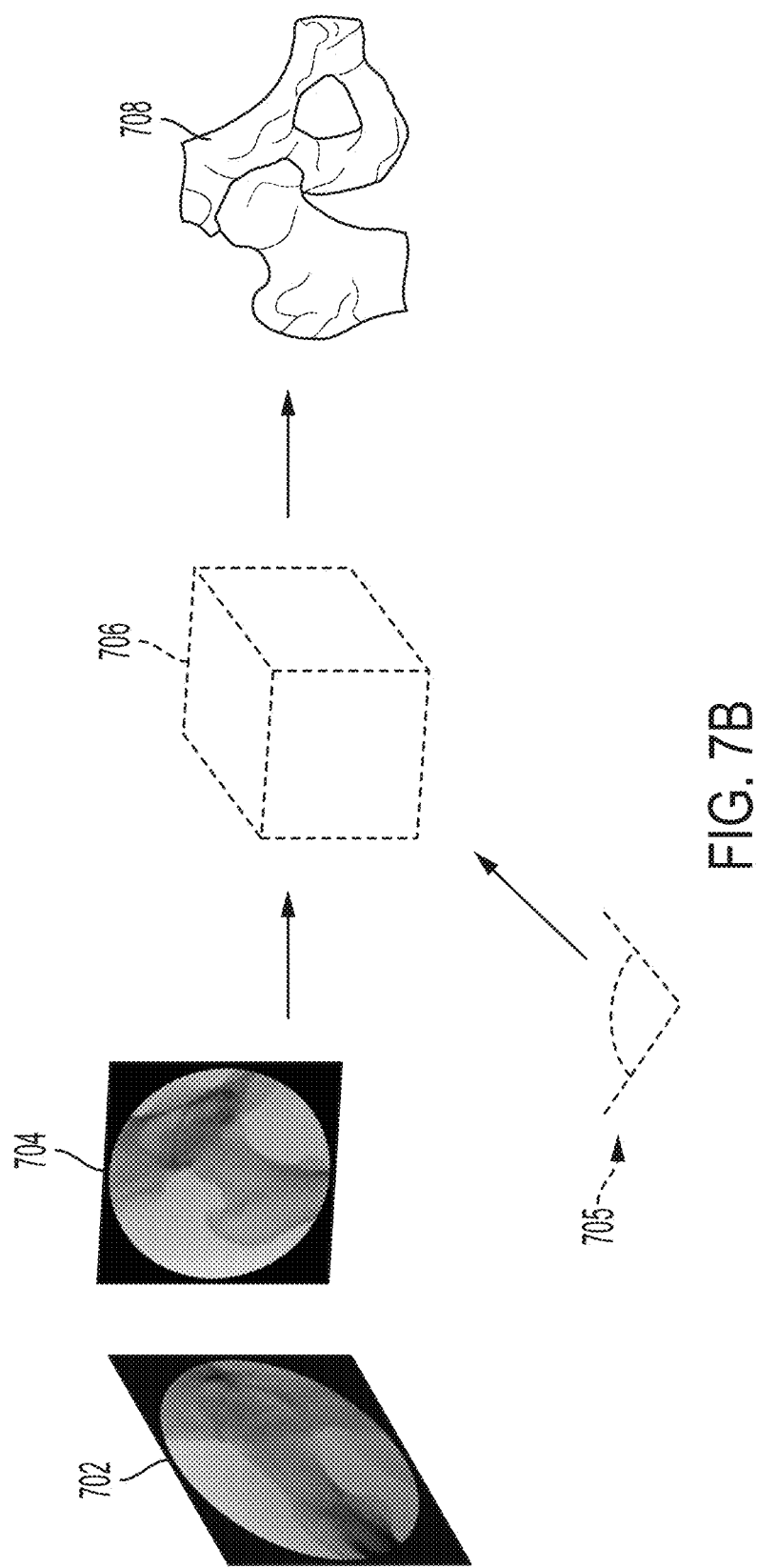
FIG. 7B illustrates an example of the transformation of two-dimensional image data into a three-dimensional model.

Step 206 results in a three-dimensional data set 207 that includes a plurality of voxels, with each voxel comprising one value for each image used to generate the three-dimensional data set 207. For n images, each voxel has n values. Thus, two two-dimensional images result in a data set 207 that includes a set of voxels that each have a first value from a first of the two images and a second value from the second of the two images, whereas three two-dimensional images result in a data set 207 that includes a set of voxels that each have a first value from a first of the three images, a second value from the second of the three images, and a third value from a third of the three images. The transformation of two-dimensional image data into three-dimensional data is illustrated in FIG. 7B. Two two-dimensional images 702 and 704 of a portion of a hip joint are transformed into three-dimensional imaging data set 706 based on image perspective information 705.

At step 208, the three-dimensional data set 207 is fed to a machine learning model that has been trained on imaging data generated via a three-dimensional imaging modality, such as Computed Tomography or Magnetic Resonance Imaging. The training of the machine learning model is discussed further below. The machine learning model is configured to generate a segmented space, which can be a set of multi-class voxels. Each voxel has as its value the class determined by the machine learning algorithm for that location in the three-dimensional space. In some examples, the classes simply correspond to "bone" and "not-bone." In other examples, the classes include particular bones. For example, for a hip joint, the classes may include "not-bone," "femur," and "pelvis." According to various examples, the output of step 208 is a multi-class voxel set 209.

At step 210, the multi-class voxel set 209 is transformed to a three-dimensional model data set. Examples of suitable three-dimensional model data set formats include STL, OBJ, FBX, COLLADA, 3DS, IGES, STEP, and VRML/X3D. The multi-class voxel set 209 can be transformed into three-dimensional model data in any suitable manner. In some examples, an iso-surface extraction technique, e.g. a Marching Cubes technique, or Marching Tetrahedra technique, is used to search the set of voxels for the surfaces of the bone(s) and generate a mesh associated with the surfaces. The output from step 210 is three-dimensional model 211 of the anatomy of interest (e.g., portion of the joint) captured in the imaging data 201. FIG. 7B illustrates the transformation of the three-dimensional data set 706 into a three-dimensional model 708 of the portion of the hip joint captured in the two-dimensional images 702 and 704. As noted above, method 200 can be applied to any anatomy of interest to generate a three-dimensional model of the anatomy of interest from two-dimensional imaging. Where the anatomy of interest is a hip joint or a portion of the hip joint, the three-dimensional model can be or include at least a head-portion of the femur, at least a portion of the acetabulum, or both. Where the anatomy of interest is a fractured bone, the three-dimensional model can include the bone in its fractured state, including any bone fragments.

Although steps 202-210 are described above with reference to two two-dimensional images, it should be understood that any number of two-dimensional images capturing any number of different perspectives may be used. For example, three, four, five, six, seven, eight, or more images from different perspectives may be used to generate the three-dimensional model. In some examples, a single image provides sufficient information to generate a three-dimensional model. According to various examples, a three-dimensional model generated according to method 200 can be combined with another three-dimensional model. For example, a three-dimensional model generated according to method 200 may more accurately capture a particular portion of the modeled anatomy and another model, such as a CT or MRI-based model may more accurately capture other portions of the modeled anatomy, and the respective portions of the models may be combined into a single model to leverage the advantages of both models.

At step 212, a visualization that is generated based on the three-dimensional model 211 is displayed for observation by a user, such as via a display associated with computing system 125 of FIG. 1. According to some examples, the three-dimensional model itself, or a portion or projection thereof, is displayed. In other examples, one or more analyses is performed via the three-dimensional model and the results of the analyses are displayed to the user.

According to some examples, one or more visualizations of at least one region of a patient that deviates from a baseline can be generated based on the three-dimensional model 211 and can assist a practitioner in planning, performing, and/or assessing the efficacy of a medical procedure, such as a surgical procedure on the at least one region of a joint. For example, a visualization of a hip joint of a subject can be provided that indicates a location of a hip joint pathology (e.g., a condition or a disorder), such as a femoroacetabular impingement, and an amount of bone that may be removed to match a baseline anatomy.

Information regarding deviations from a baseline anatomy can be generated by comparing the three-dimensional model 211 to baseline data. The baseline data can represent target joint morphology. Target joint morphology can be any joint morphology that may be desired for a given subject. Target joint morphology can be based on the anatomy representative of any reference patient population, such as a normal patient population. For example, baseline data can be a model of a "normal" joint that is derived from studies of a healthy patient population and/or from a model generated based on measurements, computer simulations, calculations, etc. The terms target, baseline, and reference are used interchangeably herein to describe joint morphology characteristics against which a subject's joint morphology is compared.

The three-dimensional model and the information regarding deviations from a baseline/target anatomy can be used to generate a three-dimensional rendering of the joint that shows the deviations from the baseline/target anatomy. Visualizations can be created that include the three-dimensional rendering and/or other information related to the subject joint. In some examples, a heat map (such as a false color map) or similar type of visualization can be generated to show difference between different three-dimensional models (e.g., before and after surgery) using different colors.

According to some examples, a physician can be provided with improved guidance with respect to the extent of a deviation of a joint morphology from a target morphology, and how much bone should be removed to achieve the target morphology, for example, during a minimally-invasive arthroscopic procedure or open surgical procedure. According to some examples, visualizations can provide a physician with improved guidance with respect to morphology measurements for a hip joint, including the Alpha Angle, Lateral Center Edge Angle, Acetabular Version and Femoral Torsion, Tönnis angle, neck shaft angle, and acetabular coverage that can help a practitioner gauge a deviation of the subject morphology from a target morphology. In some example, one or more of these measurements or any other measurement may be provided in a visualization, such as overlaid on a rendering of the three-dimensional model.

Figure 10A:
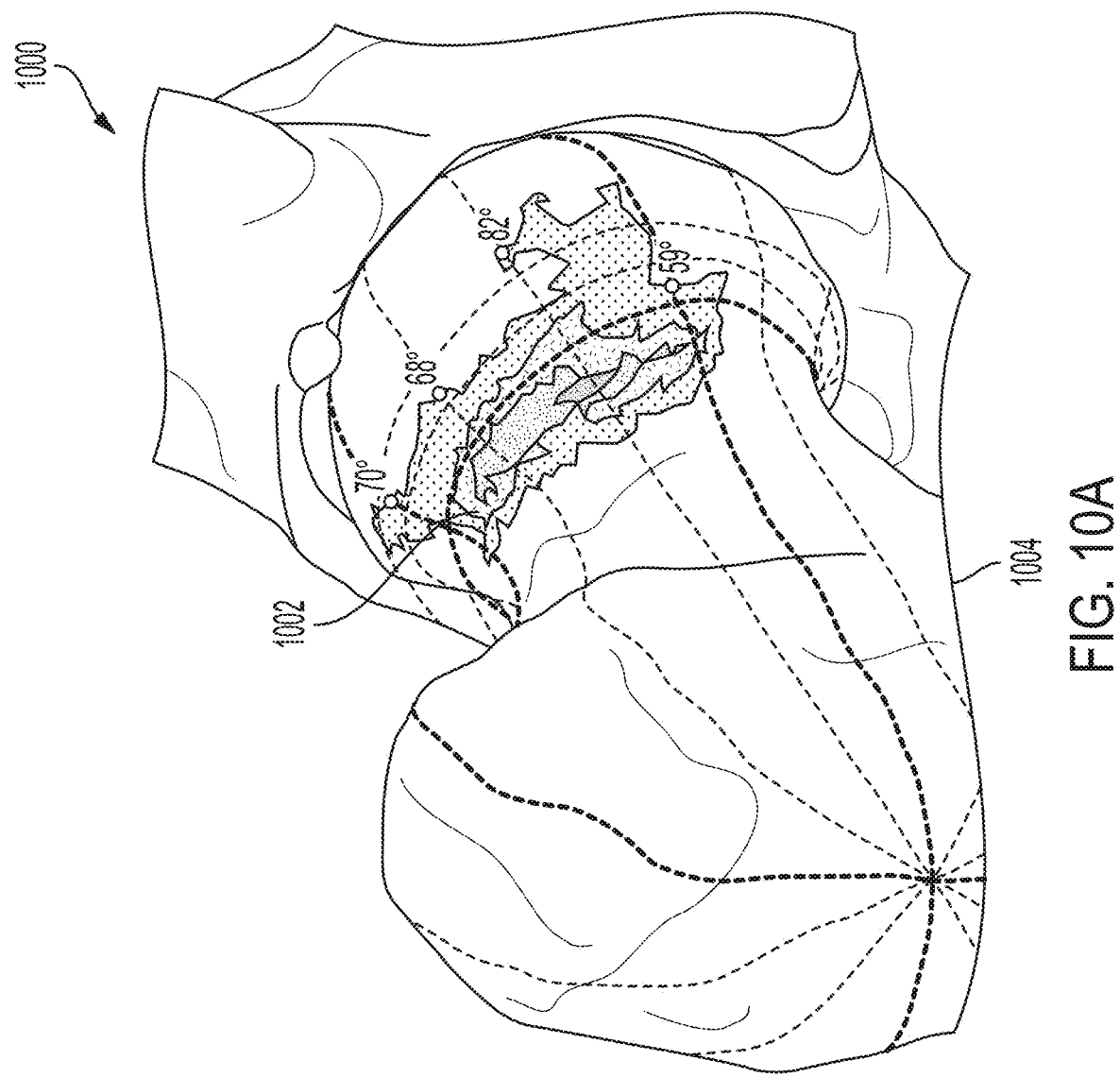
FIG. 10A is an exemplary illustration of a visualization of a three-dimensional model.
Figure 10B:
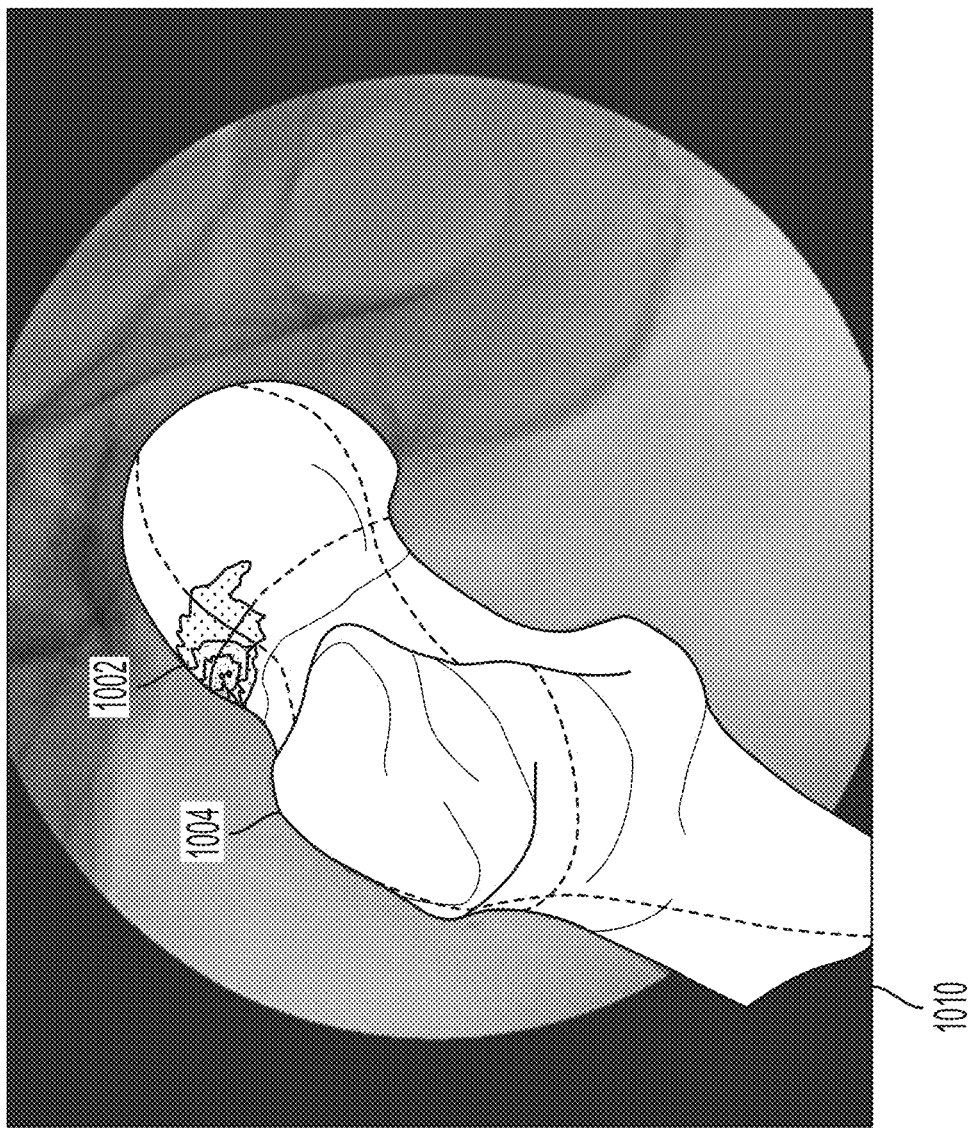
FIG. 10B is an exemplary illustration of an overlay of a visualization of a three-dimensional model on an X-ray image.

FIG. 10A is an exemplary illustration of a visualization 1000 provided in step 212 of method 200, according to some examples. A heat map 1002 has been generated based on the three-dimensional model to show where and how much bone should be removed to treat a pathology associated with a hip joint of a patient, and the heat map 1002 is provided as an overlay on a rendering 1004 of the three-dimensional model. The heat map 1002 is generated based on measurements from the model and comparisons of those measurements from target morphology, as discussed above. Other visualizations of target bone removal can include a contour map, or a spline provided on a two-dimensional representation of the anatomy of interest generated from the three-dimensional model. In some examples, a visualization generated from the three-dimensional model can be provided along with a two-dimensional image generated during a medical procedure. For example, a rendering of the three-dimensional model or a heat map or contour map generated from the three-dimensional model may be overlaid on an X-ray image. The X-ray image may be continuously obtained and displayed in real-time. An example of such an overlay is illustrated in FIG. 10B in which rendering 1004 with heat map 1002 is overlaid on X-ray image 1010.

A visualization provided in step 212 could additionally or alternatively include one or more indications of one or more anatomical landmarks. For example, the visualization could include the model and labels for one or more anatomical landmarks on the model. Landmarks can be identified in the model using a statistical shape model/atlas or a machine learning algorithm.

In some examples, method 200 is performed pre-operatively, such as during an out-patient procedure, to generate a pre-operative plan. In some examples, method 200 is performed just prior to the start of a procedure, such as just prior to the start of a surgical procedure, to generate a plan for the procedure and/or to update an existing plan. In some examples, method 200 is performed during a procedure, such as a surgical or a non-surgical procedure to assess the progress of the procedure. In some examples, the three-dimensional model generated during the procedure can be compared to a previously generated model to assess differences in the anatomy of the patient resulting from the procedure. For example, where the procedure involves bone removal, a three-dimensional model can be generated after bone has been removed and the three-dimensional model can be compared to a previously-generated three-dimensional model to determine where and how much bone has been removed. This information can be provided to the practitioner, such as part of a visualization. Three-dimensional models can be generated or updated repeatedly during a procedure to assist the practitioner in tracking the progress of the procedure, such as for tracking the progress of bone removal. For example, in trauma cases where fragmented bone is removed, three-dimensional models can be generated or updated repeatedly so that the practitioner can track which fragments have been removed. Three-dimensional models can be generated or updated repeatedly during a procedure when, for example, the anatomy of interest has moved over time during the procedure.

In some examples, a three-dimensional model is updated during a procedure based on new imaging data. For example, a three-dimensional model may be generated at the start of a procedure based on two-dimensional images generated at the start of the procedure and the three-dimensional model may be updated and/or refined when new two-dimensional images are generated as the procedure progresses. In some examples, a three-dimensional model is generated from newly captured two-dimensional images in combination with previously captured two-dimensional images. For example, an initial set of images may be used to generate a first three-dimensional model, a new set of images may be captured, and a second three-dimensional model may be generated from the new set of images in combination with one or more images from the initial set of images. In some examples, a three-dimensional model generated from two-dimensional images is combined with another three-dimensional model. For example, a three-dimensional model may be generated pre-operatively, such as from a CT scan or an MRI scan, and the three-dimensional model may be updated based on a three-dimensional model generated from two-dimensional images during the procedure, according to the principles discussed above. This could be useful for updating the pre-operatively generated three-dimensional model to reflect changes in anatomy of the patient, such as due to bone removing, that are captured intra-operatively via the two-dimensional imaging.

In some examples, a user, such as a surgeon, can tailor the visual representation of step 212 for surgical planning or performance purposes, such as by altering one or more parameters that determine the deviations from the target bone morphology, which can increase or decrease the size of the region indicated for bone removal and/or increase or decrease the amount of bone indicated for removal.

Figure 8:
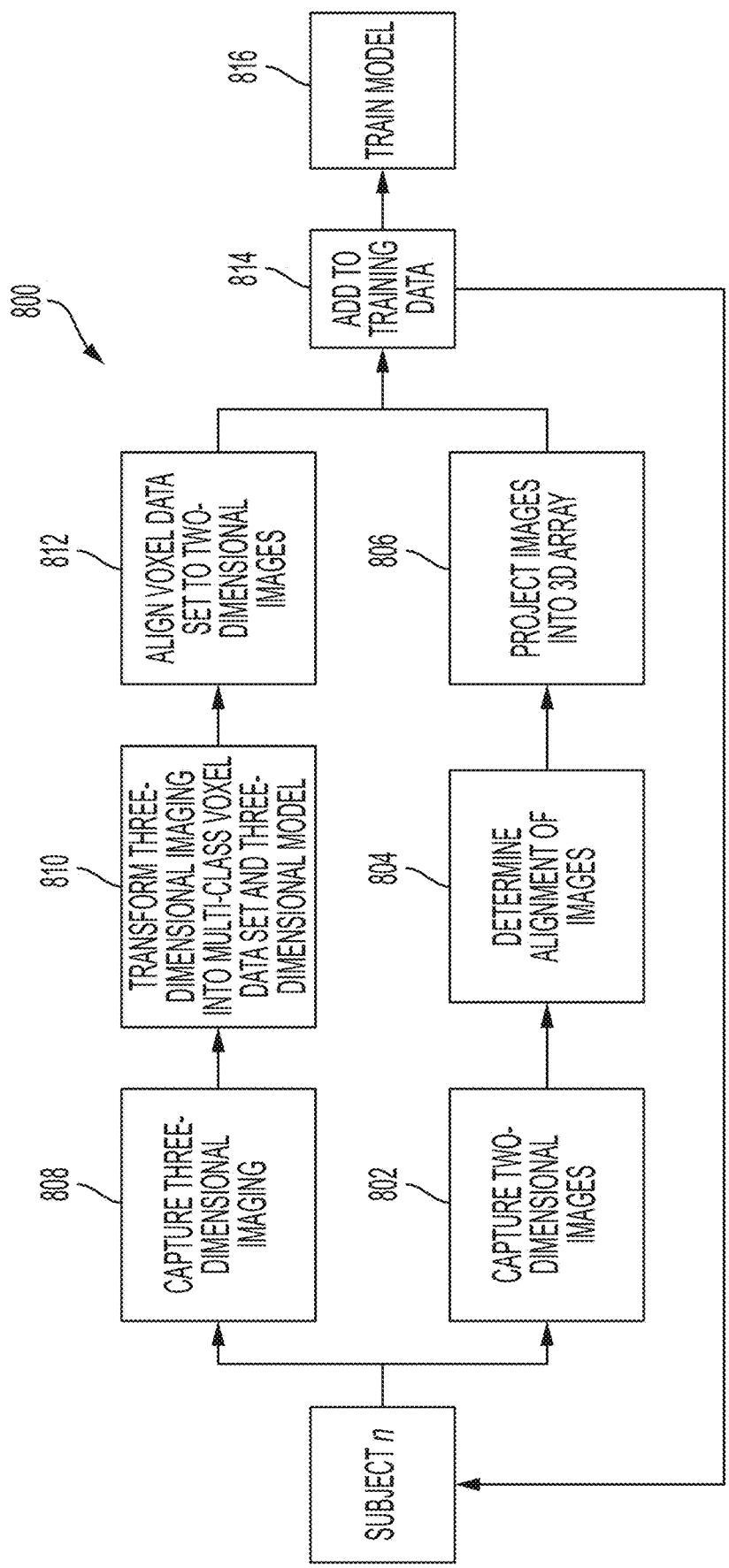
FIG. 8 is a block diagram of an exemplary method for training a machine learning model that can generate a three-dimensional model from two-dimensional images.

FIG. 8 is a block diagram of a method 800 for training a machine learning model for use in step 208 of method 200, according to some examples. At step 802, a two-dimensional imaging modality is used to generate at least two two-dimensional images (e.g., X-ray images) of a subject n are captured from two different perspectives. For example, a first X-ray image may capture an anterior-posterior view of the subject's hip joint and a second X-ray image may capture a lateral view of the same hip joint. At step 804, the alignment between the images is determined. This step can be performed in similar fashion to step 204 of method 200 discussed above. At step 806, the images are back-projected into three-dimensional space based on the alignment determined at step 804. This step can be performed in similar fashion to step 206 of method 200.

At step 808, a three-dimensional imaging modality is used to generate three-dimensional imaging data of the same portion of the subject captured in the two-dimensional images. The three-dimensional imaging modality can be, for example, CT imaging or MM imaging. At step 810, the three-dimensional imaging data from step 808 is transformed into a three-dimensional model (e.g., using an STL format) by a manual/semiautomated/automated segmentation step which extracts the 3D surface and a multi-class voxel data set containing the respective voxels inside that surface. At step 812, the three-dimensional model is used to align the multi-class voxel data set to the two-dimensional imaging data set from step 806, which can be done in various ways. For example, the alignment can be done manually, such as by a user, based on the two-dimensional imaging and the three-dimensional model, or the alignment can be done automatically based on automatic identification of one or more anatomical features or fiducials in the images and in the three-dimensional model and comparing the position and orientation of the feature(s). For example, one or more features in the two-dimensional images can be used to register the two-dimensional images with the three-dimensional model. In some examples, a two-dimensional outline that is manually or automatically segmented from a two-dimensional image can be aligned to the three-dimensional model and this registration can be used to align the two-dimensional image to the three-dimensional model.

The back-projected image data from step 806 and the aligned multi-class voxel data from step 812 is added to the machine learning model training data step at step 814. Steps 802-814 are repeated for each subject. Steps 802 and 808 can include generating the imaging data, as described above, or receiving the image data that was previously generated.

At step 816, the machine learning model is trained on the training data. The machine learning model is configured to transform the three-dimensional array of two-dimensional imaging data into a set of multi-class voxels, where the multi-class voxel data set from steps 810 and 812 serves as the target for the machine learning model for the corresponding two-dimensional imaging data. The machine learning model can include any suitable machine learning technique or combination of techniques, including, for example, a convolutional neural network. Once trained, the machine learning model can be used in step 208 of method 200.

The trained machine learning model resulting from method 800 may be configured for generating a model of a particular region of the body. For example, the machine learning model may be configured for modeling the hip joint, the knee joint, one or more vertebral joints of the spine, a shoulder joint, etc. In some examples, the trained machine learning model can model multiple regions of the body, such as hip joints, knee joints, shoulder joints, etc. This can be achieved, for example, by including imaging data for these different regions in the training data.

Figure 9:
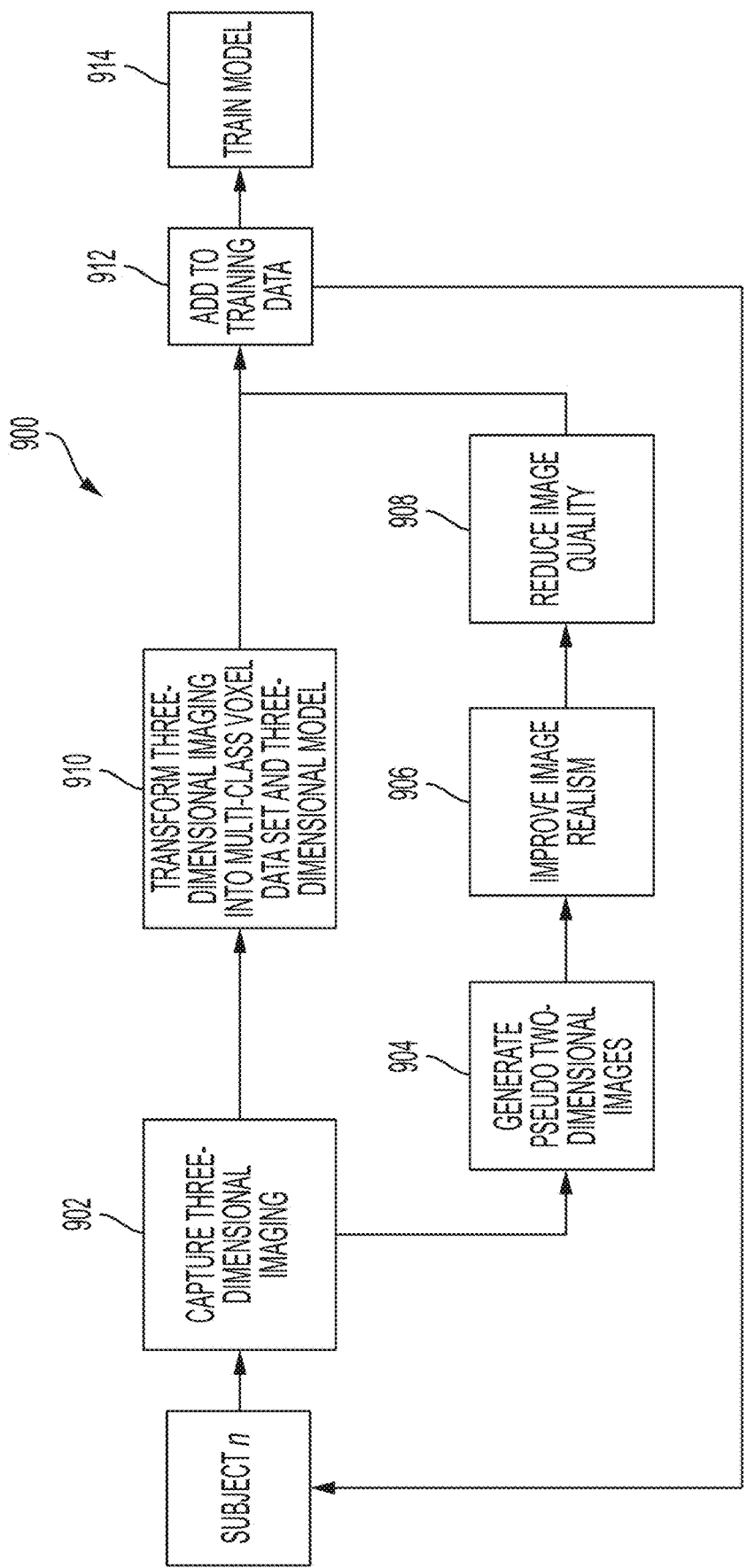
FIG. 9 is a block diagram of an example of an alternative method for training a machine learning model that can generate a three-dimensional model from two-dimensional images.

FIG. 9 is a block diagram of an alternative method 900 for training a machine learning model for use in step 208 of method 200, according to some examples. In contrast to method 800, which uses two-dimensional imaging modality imaging data in combination with three-dimensional imaging modality imaging data, method 900 uses three-dimensional imaging modality data to generate pseudo two-dimensional imaging data that seek to approximate two-dimensional imaging modality images. The pseudo two-dimensional imaging modality imaging data can be, for example, digitally reconstructed radiographs (DRR) or any other data set. For example, DRRs can be generated from a CT scan. The pseudo two-dimensional imaging data is then used in similar fashion to the two-dimensional imaging modality imaging in method 800, as described further below.

At step 902, three-dimensional imaging modality imaging data is generated for a subject. The three-dimensional imaging modality can be, for example, CT or MRI. Any portion of the subject may be imaged. According to various examples, a hip joint, a knee joint, a shoulder joint, an elbow joint, vertebral joints, an ankle, or any other region of the subject's body is imaged. According to some examples, step 902 includes receiving pre-captured three-dimensional imaging data.

At step 904, the three-dimensional imaging data is used to generate pseudo two-dimensional images capturing the region of interest from different perspectives by flattening the three-dimensional imaging data according to known methods. At step 906, the pseudo two-dimensional images are altered to make them look more like actual two-dimensional imaging images. For example, a generative adversarial network (GAN) or a style transfer can be used to generate two-dimensional images that are more similar to actual two-dimensional imaging modality images.

At step 906, the more realistic pseudo two-dimensional images from step 904 are altered to reduce image quality, again, to make the pseudo two-dimensional images more like actual two-dimensional images. This step can include increasing or decreasing contrast, adding noise to the data, adding artifacts to the images, such as to mimic a tool being in the field of view.

At step 908, the pseudo two-dimensional images that have been transformed via steps 904 and 906 are back-projected into three-dimensional space in similar fashion to step 206 of method 200, except that the difference in perspectives between the pseudo two-dimensional images is precisely known. In some examples, a degree of misalignment is introduced at this step to approximate alignment errors that are likely to occur when using real two-dimensional images in method 200.

At step 910, the three-dimensional imaging data from step 902 is transformed into a three-dimensional model (e.g., using an STL format) and a multi-class voxel data set in similar fashion to step 810 of method 800. At step 912, the back-projected three-dimensional imaging data from step 908 and the multi-class voxel data set from step 910 are added to the training data set. Steps 902-912 can be repeated to generate additional training data. In some examples, the same set of three-dimensional imaging data (e.g., the same CT or MRI scan data) is used multiple times, where each time generates a different set of pseudo two-dimensional images. Once the training data set is complete, the machine learning algorithm is trained at step 914 in similar fashion to step 816 of method 800.

Figure 11:
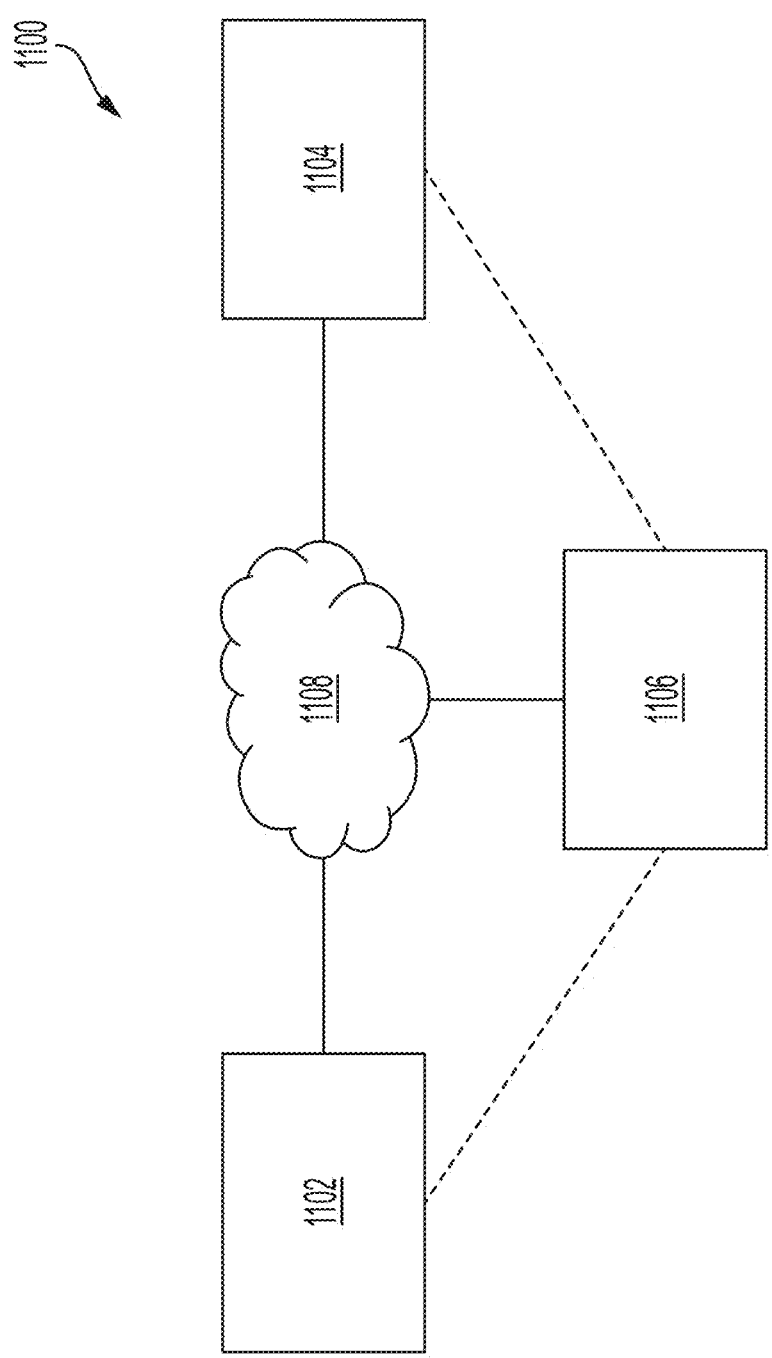
FIG. 11 illustrates a system for generating a three-dimensional model from two-dimensional imaging.

FIG. 11 illustrates a system 1100 for generating a three-dimensional model of a portion of a subject from two-dimensional imaging, according to various examples. System 1100 can include a machine learning model generation subsystem 1102 for generating a machine learning model that can generate a three-dimensional model from two-dimensional imaging data. System 1100 can include an imaging subsystem 1104 for generating two-dimensional images fed to the machine learning model generated by subsystem 1102. The imaging subsystem can be an intra-operative imaging system such as C-arm X-ray machine 115 of FIG. 1, for intra-operatively generating two-dimensional images during a surgical procedure. System 1100 includes a model generation and visualization subsystem 1106, such as computing system 125 of FIG. 1, for generating a three-dimensional model from two-dimensional images generated by imaging subsystem 1104 and visualizations based on the three-dimensional model. The subsystems may be communicatively connected to one another via one or more communication connections 1108, which can be a network connection, such as a local area network, a wide area network, a combination of local and wide area networks, or any suitable communication network, one or more direct connections between the subsystems, or a combination of direct and network connections. Any of the machine learning model generating subsystem 1102, the imaging subsystem 1104, and the visual guidance subsystem 1106 can be in separate locations from the other subsystems or can have components that are in separate locations from the other subsystems or components of subsystems. In some examples, two or more of the subsystems or portions of the subsystems may be in the same location, such as in the same operating suite. In some examples, the model generation and visualization subsystem 1106 and the imaging subsystem 1104 are the same system or share the same components, such as the same imager. In some examples, a machine learning model generated by machine learning model generating subsystem 1102 is hardcoded into model generation and visualization subsystem 1106.

The machine learning model generation subsystem 1102 can include one or more imagers for generating imaging data for a subject. Imaging data can include, for example, MRI scans, CT scans, X-ray radiographs, fluoroscopic images, fluorescence imaging data, or any suitable imaging data for imaging anatomy of a subject. In some examples, the machine learning model generation subsystem 1102 can include one or more imaging data processing systems for processing imaging data generated by an imager. The machine learning model generation subsystem 1102 can include one or more data storage systems for storing imaging data and/or model data.

Imaging subsystem 1104 can include an imager for generating two-dimensional imaging data for a subject, which can be done in a pre-procedural planning stage, just prior to the start of a medical procedure, during the medical procedure, or after the medical procedure has been completed. The imaging subsystem 1104 can include, for example, an X-ray imager, such as a C-arm fluoroscopic imager. In some examples, the imaging subsystem 1104 can be configured to transmit imaging data for a subject to model generation and visualization subsystem 1106. For example, upon capturing an image of the anatomy of interest of the subject, the image can be transmitted to the model generation and visualization subsystem 1106 for generating a three-dimensional model and one or more visualizations, according to the principles described herein.

Model generation and visualization subsystem 1106 can generate a three-dimensional model from two-dimensional images, as described above. In some examples, subsystem 1106 can identify at least one region of imaged anatomy that deviates from a baseline anatomy by comparing at least a portion of the three-dimensional model to a baseline model. The subsystem 1102 can generate one or more measurements of a characteristic of the anatomy at one or more predefined locations using the three-dimensional model and a coordinate system; and can generate a three-dimensional visual rendering of the model, according to the principles described herein. The three-dimensional rendering can include a visual indication of the at least one region of the three-dimensional model that deviates from the baseline, wherein the at least one region is visually indicated according to degree of deviation. This visual indication can represent planned bone removal for a surgical procedure. The three-dimensional rendering can be a component of a visualization that includes any other relevant information as described herein.

Figure 12:
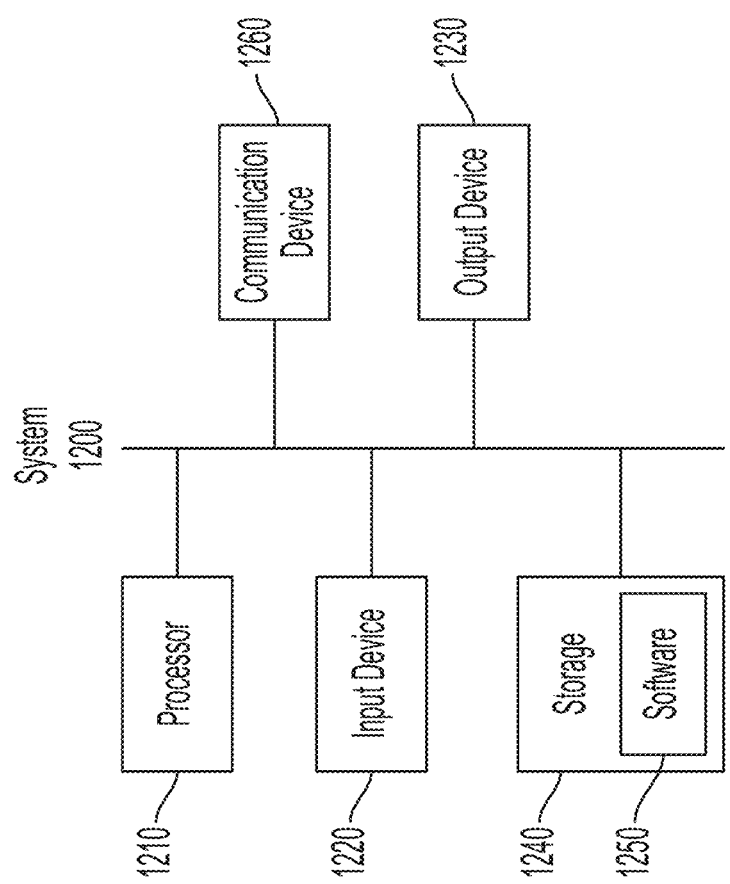
FIG. 12 illustrates an example of a computing system.

FIG. 12 illustrates an example of a computing system, in accordance with some examples, that can be used for one or more of subsystems 1102, 1104, and 1106 of system 1100. System 1200 can be a computer connected to a network, such as one or more networks of communication connections 1108 of system 1100. System 1200 can be a client computer or a server. As shown in FIG. 12, system 1200 can be any suitable type of microprocessor-based system, such as a personal computer, workstation, server, or handheld computing device (portable electronic device) such as a phone or tablet. The system can include, for example, one or more of processor 1210, input device 1220, output device 1230, storage 1240, and communication device 1260. Input device 1220 and output device 1230 can generally correspond to those described above and can either be connectable or integrated with the computer.

Input device 1220 can be any suitable device that provides input, such as a touch screen, keyboard or keypad, mouse, gesture recognition component of a virtual/augmented reality system, or voice-recognition device. Output device 1230 can be or include any suitable device that provides output, such as a touch screen, haptics device, virtual/augmented reality display, or speaker.

Storage 1240 can be any suitable device that provides storage, such as an electrical, magnetic, or optical memory including a RAM, cache, hard drive, removable storage disk, or other non-transitory computer readable medium. Communication device 1260 can include any suitable device capable of transmitting and receiving signals over a network, such as a network interface chip or device. The components of the computer can be connected in any suitable manner, such as via a physical bus or wirelessly.

Software 1250, which can be stored in storage 1240 and executed by processor 1210, can include, for example, the programming that embodies the functionality of the present disclosure (e.g., as embodied in the devices as described above). For example, software 1250 can include one or more programs for performing one or more of the steps of method 200, method 800, and/or method 900.

Software 1250 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1240, that can contain or store programming for use by or in connection with an instruction execution system, apparatus, or device.

Software 1250 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

System 1200 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1200 can implement any operating system suitable for operating on the network. Software 1250 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated. For the purpose of clarity and a concise description, features are described herein as part of the same or separate examples; however, it will be appreciated that the scope of the disclosure includes examples having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference. For the purpose of clarity and a concise description, features are described herein as part of the same or separate examples; however, it will be appreciated that the scope of the disclosure includes examples having combinations of all or some of the features described.

The invention claimed is:

1. A method for modeling at least a portion of a joint before, during and/or after a medical procedure, the method comprising:
    receiving first imaging data capturing the at least a portion of the joint from a first imaging perspective and second imaging data capturing the at least a portion of the joint from a second imaging perspective that is different than the first imaging perspective, the first and second imaging data generated via a two-dimensional imaging modality;
    generating three-dimensional image data by back-projecting the first and second imaging data in three-dimensional space in accordance with a relative difference between the first and second imaging perspectives;
    generating a three-dimensional model of the at least a portion of the joint by:
        generating a set of multi-class voxels by processing the three-dimensional image data with a machine learning model trained on imaging data generated via at least a three-dimensional imaging modality; and
        generating the three-dimensional model of the at least a portion of the joint based on multi-class voxels of the set of multi-class voxels that correspond to at least one class associated with the at least a portion of the joint; and
    displaying a visualization based on the three-dimensional model of the at least a portion of the joint during the medical procedure.

2. The method of claim 1, wherein the two-dimensional imaging modality is C-arm fluoroscopy.

3. The method of claim 1, wherein the three-dimensional imaging modality is computed tomography or magnetic resonance imaging.

4. The method of claim 1, wherein generating the three-dimensional image data comprises aligning the first and second imaging data based on the relative difference between the first and second imaging perspectives.

5. The method of claim 4, comprising determining the relative difference between the first and second imaging perspectives based on analyzing the first and second imaging data.

6. The method of claim 5, wherein the relative difference between the first and second imaging perspectives is determined based on at least one fiducial captured in the first and second imaging data.

7. The method of claim 6, wherein the at least one fiducial corresponds to at least one object located within a field of view, and the relative difference between the first and second imaging perspectives is determined based on a predetermined geometry of the at least one object.

8. The method of claim 5, wherein determining the relative difference between the first and second imaging perspectives comprises identifying at least one feature of the at least a portion of the joint in the first and second imaging data and determining the relative difference between the first and second imaging perspectives based on a position of the at least one feature in the first imaging data and a position of the at least one feature in the second imaging data.

9. The method of claim 1, wherein each multi-class voxel represents bone or no-bone.

10. The method of claim 1, wherein the machine learning model was trained using training images generated via the two-dimensional imaging modality.

11. The method of claim 10, wherein the machine learning model was trained using multi-class voxel arrays that are based on training data generated via the three-dimensional imaging modality.

12. The method of claim 11, wherein the machine learning model was trained via the multi-class voxel arrays aligned to the training images generated via the two-dimensional imaging modality.

13. The method of claim 1, wherein the machine learning model was trained on two-dimensional image data generated from three-dimensional imaging modality imaging data.

14. The method of claim 1, comprising receiving third imaging data capturing the at least a portion of the joint from a third imaging perspective and generating the three-dimensional image data based on the first, second, and third imaging data.

15. The method of claim 1, wherein the visualization comprises a rendering of at least a portion of the three-dimensional model.

16. The method of claim 1, wherein the visualization comprises one or more measurements generated based on the three-dimensional model.

17. The method of claim 1, comprising removing bone during the medical procedure, wherein the three-dimensional model reflects removed bone.

18. The method of claim 1, wherein the visualization comprises a representation of target bone removal.

19. The method of claim 18, wherein the representation of target bone removal comprises at least one of a heat map and a contour map.

20. A system comprising one or more processor, memory, and one or more programs stored in the memory and configured for execution by the one or more processors for:
receiving first imaging data capturing at least a portion of a joint from a first imaging perspective and second imaging data capturing the at least a portion of the joint from a second imaging perspective that is different than the first imaging perspective, the first and second imaging data generated via a two-dimensional imaging modality;
generating three-dimensional image data by back-projecting the first and second imaging data in three-dimensional space in accordance with a relative difference between the first and second imaging perspectives;
generating a three-dimensional model of the at least a portion of the joint by:
generating a set of multi-class voxels by processing the three-dimensional image data with a machine learning model trained on imaging data generated via at least a three-dimensional imaging modality; and
generating the three-dimensional model of the at least a portion of the joint based on multi-class voxels of the set of multi-class voxels that correspond to at least one class associated with the at least a portion of the joint; and
displaying a visualization based on the three-dimensional model of the at least a portion of the joint during the medical procedure.

21. The system of claim 20, wherein the two-dimensional imaging modality is C-arm fluoroscopy.

22. The system of claim 20, wherein the three-dimensional imaging modality is computed tomography or magnetic resonance imaging.

23. The system of claim 20, wherein generating the three-dimensional image data comprises aligning the first and second imaging data based on the relative difference between the first and second imaging perspectives.

24. The system of claim 23, wherein the one or more programs include instructions for determining the relative difference between the first and second imaging perspectives based on analyzing the first and second imaging data.

25. The system of claim 24, wherein the relative difference between the first and second imaging perspectives is determined based on at least one fiducial captured in the first and second imaging data.

26. The system of claim 25, wherein the at least one fiducial corresponds to at least one object located within a field of view, and the relative difference between the first and second imaging perspectives is determined based on a predetermined geometry of the at least one object.

27. The system of claim 24, wherein determining the relative difference between the first and second imaging perspectives comprises identifying at least one feature of the at least a portion of the joint in the first and second imaging data and determining the relative difference between the first and second imaging perspectives based on a position of the at least one feature in the first imaging data and a position of the at least one feature in the second imaging data.

28. The system of claim 20, wherein each multi-class voxel represents bone or no-bone.

29. A non-transitory computer readable medium storing one or more programs for execution by one or more processors of a computing system for:
receiving first imaging data capturing the at least a portion of the joint from a first imaging perspective and second imaging data capturing the at least a portion of the joint from a second imaging perspective that is different than the first imaging perspective, the first and second imaging data generated via a two-dimensional imaging modality;
generating three-dimensional image data by back-projecting the first and second imaging data in three-dimensional space in accordance with a relative difference between the first and second imaging perspectives;
generating a three-dimensional model of the at least a portion of the joint by:
generating a set of multi-class voxels by processing the three-dimensional image data with a machine learning model trained on imaging data generated via at least a three-dimensional imaging modality; and
generating the three-dimensional model of the at least a portion of the joint based on multi-class voxels of the set of multi-class voxels that correspond to at least one class associated with the at least a portion of the joint; and
displaying a visualization based on the three-dimensional model of the at least a portion of the joint during the medical procedure.

* * * * *